(12) United States Patent
Reddy et al.

(10) Patent No.: US 10,493,228 B2
(45) Date of Patent: Dec. 3, 2019

(54) POSITIVE PRESSURE VENTILATION APPLIANCE MODULES AND RELATED SYSTEMS AND METHODS

(71) Applicant: ReddyPort Inc., Salt Lake City, UT (US)

(72) Inventors: Chakravarthy B. Reddy, Salt Lake City, UT (US); Joseph Orr, Salt Lake City, UT (US); Rian Wendling, Salt Lake City, UT (US); Andrew S. Hansen, Salt Lake City, UT (US)

( * ) Notice: Subject to any disclaimer, the term of this patent is extended or adjusted under 35 U.S.C. 154(b) by 0 days.

(21) Appl. No.: 16/197,201

(22) Filed: Nov. 20, 2018

(65) Prior Publication Data

US 2019/0091434 A1    Mar. 28, 2019

Related U.S. Application Data

(63) Continuation of application No. 15/870,107, filed on Jan. 12, 2018, which is a continuation-in-part of
(Continued)

(51) Int. Cl.
*A61M 16/06*        (2006.01)
*A61M 16/08*        (2006.01)
(Continued)

(52) U.S. Cl.
CPC .... *A61M 16/0841* (2014.02); *A61M 16/0057* (2013.01); *A61M 16/024* (2017.08);
(Continued)

(58) Field of Classification Search
CPC ....... A61B 1/00154; A61B 1/01; A61B 1/267; A61B 1/2676; A61B 1/2736; A61B 5/082; A61B 5/097; A61B 7/023; A61J 15/0003; A61J 15/0053; A61M 1/0043; A61M 11/00; A61M 11/06; A61M 15/009; A61M 16/0003; A61M 16/0048; A61M 16/0057;
(Continued)

(56) References Cited

U.S. PATENT DOCUMENTS 2,625,155 A  *  1/1953  Engelder .............. A61M 16/06
                                              128/206.24
4,212,300 A  *  7/1980  Meals ................. A61M 1/0043
                                              15/344

(Continued)

FOREIGN PATENT DOCUMENTS

WO    WO 2015/054747       4/2015
WO    WO2017021836 A1      2/2017

OTHER PUBLICATIONS

VBM Medizintechnik GmbH, VBM Endoscopy Mask, 2 pages, P326-6.0GB/03.14.

*Primary Examiner* — Annette Dixon
(74) *Attorney, Agent, or Firm* — Alpine IP PLLC

(57) ABSTRACT

A positive pressure ventilation (PPV) appliance module includes an adapter that couples to a port on an NIV mask and an appliance for performing a respiratory care procedure. The adapter is configured to form a PPV seal with the port of the PPV mask and also form a PPV seal with the appliance. The PPV appliance module allows clinicians to perform procedures through the NIV mask without disrupting the therapeutic pressure.

20 Claims, 16 Drawing Sheets

Related U.S. Application Data application No. PCT/US2017/060480, filed on Nov. 7, 2017, which is a continuation-in-part of application No. PCT/US2016/039117, filed on Jun. 23, 2016.

(60) Provisional application No. 62/568,314, filed on Oct. 4, 2017, provisional application No. 62/418,787, filed on Nov. 7, 2016, provisional application No. 62/252,577, filed on Nov. 8, 2015, provisional application No. 62/183,733, filed on Jun. 23, 2015.

(51) Int. Cl.
*A61M 16/04* (2006.01)
*A61M 16/20* (2006.01)
*A61M 16/00* (2006.01)
*A61M 16/14* (2006.01)
*A61M 39/02* (2006.01)

(52) U.S. Cl.
CPC ...... *A61M 16/049* (2014.02); *A61M 16/0463* (2013.01); *A61M 16/06* (2013.01); *A61M 16/0683* (2013.01); *A61M 16/0816* (2013.01); *A61M 16/0858* (2014.02); *A61M 16/14* (2013.01); *A61M 16/20* (2013.01); *A61M 16/208* (2013.01); *A61M 39/02* (2013.01); *A61M 2205/502* (2013.01); *A61M 2230/432* (2013.01)

(58) Field of Classification Search
CPC .......... A61M 16/0078; A61M 16/0084; A61M 16/01; A61M 16/024; A61M 16/0409; A61M 16/0415; A61M 16/0427; A61M 16/0461; A61M 16/0463; A61M 16/0465; A61M 16/047; A61M 16/0486; A61M 16/0488; A61M 16/0493; A61M 16/0495; A61M 16/0497; A61M 16/06; A61M 16/0605; A61M 16/0616; A61M 16/0683; A61M 16/08; A61M 16/0816; A61M 16/0825; A61M 16/0833; A61M 16/0841; A61M 16/085; A61M 16/0866; A61M 16/0875; A61M 16/12; A61M 16/125; A61M 16/14; A61M 16/16; A61M 16/20; A61M 16/208; A61M 2016/0661; A61M 2202/0208; A61M 2202/0241; A61M 2202/0283; A61M 2205/05; A61M 2205/11; A61M 2205/502; A61M 2209/06; A61M 2210/005; A61M 2210/0618; A61M 2210/0625; A61M 2210/1053; A61M 2230/202; A61M 2230/43; A61M 2230/432; A61M 39/02; A62B 18/025; A62B 18/10; A62B 23/025; Y10S 128/26; Y10S 128/911; Y10S 128/912; Y10S 604/905

See application file for complete search history.

(56) References Cited

U.S. PATENT DOCUMENTS

| | | | |
|---|---|---|---|
| 5,027,811 A * | 7/1991 | Tuxill | A61M 16/0465 128/207.14 |
| 5,062,420 A * | 11/1991 | Levine | A61M 16/08 128/204.18 |
| 5,085,633 A * | 2/1992 | Hanifl | A61C 17/043 29/450 |
| 5,184,611 A * | 2/1993 | Turnbull | A61M 16/0463 128/200.26 |
| 5,197,463 A * | 3/1993 | Jeshuran | A61M 16/0463 128/206.28 |
| 5,431,158 A * | 7/1995 | Tirotta | A61M 16/0488 128/200.26 |
| 5,465,712 A * | 11/1995 | Malis | A61M 16/06 128/203.11 |
| 5,694,929 A * | 12/1997 | Christopher | A61M 16/0488 128/205.25 |
| 5,957,127 A | 9/1999 | Yamamori et al. | |
| 6,129,547 A | 10/2000 | Cise et al. | |
| 6,386,198 B1 * | 5/2002 | Rugless | A62B 18/10 128/205.25 |
| D464,728 S | 10/2002 | Paul et al. | |
| 6,513,526 B2 | 2/2003 | Kwok et al. | |
| 6,615,835 B1 | 9/2003 | Cise et al. | |
| 6,632,091 B1 | 10/2003 | Cise et al. | |
| 6,792,943 B2 | 9/2004 | Kumar et al. | |
| 8,146,591 B2 | 4/2012 | Niklewski et al. | |
| 8,302,605 B2 | 11/2012 | Edwards et al. | |
| 8,365,734 B1 * | 2/2013 | Lehman | A61M 16/0078 128/200.24 |
| 8,616,195 B2 | 12/2013 | Power et al. | |
| 9,119,931 B2 | 9/2015 | D'souza et al. | |
| 9,186,474 B1 * | 11/2015 | Rollins, III | A61M 16/0605 |
| 9,295,799 B2 | 3/2016 | McAuley et al. | |
| 2003/0024533 A1 * | 2/2003 | Sniadach | A61M 16/06 128/205.25 |
| 2003/0047189 A1 * | 3/2003 | Kumar | A61M 16/0488 128/206.29 |
| 2005/0245836 A1 | 11/2005 | Star et al. | |
| 2007/0199567 A1 * | 8/2007 | Kanzer | A62B 18/025 128/206.21 |
| 2007/0244426 A1 | 10/2007 | Hart et al. | |
| 2008/0053449 A1 * | 3/2008 | Lindblom | A61M 16/0488 128/206.21 |
| 2009/0007357 A1 | 1/2009 | Meadows et al. | |
| 2009/0143645 A1 * | 6/2009 | Matthes | A61M 1/267 600/120 |
| 2010/0116276 A1 | 5/2010 | Bayasi | |
| 2012/0272962 A1 | 11/2012 | Doyle et al. | |
| 2012/0285465 A1 | 11/2012 | Pierro et al. | |
| 2013/0172768 A1 * | 7/2013 | Lehman | A61M 16/085 600/532 |
| 2014/0076311 A1 * | 3/2014 | Darab | A61M 16/06 128/203.12 |
| 2017/0035979 A1 | 2/2017 | Pedro et al. | |
| 2018/0133429 A1 * | 5/2018 | Reddy | A61M 16/0841 |
| 2018/0361102 A1 * | 12/2018 | Wendling | A61M 39/02 |

* cited by examiner

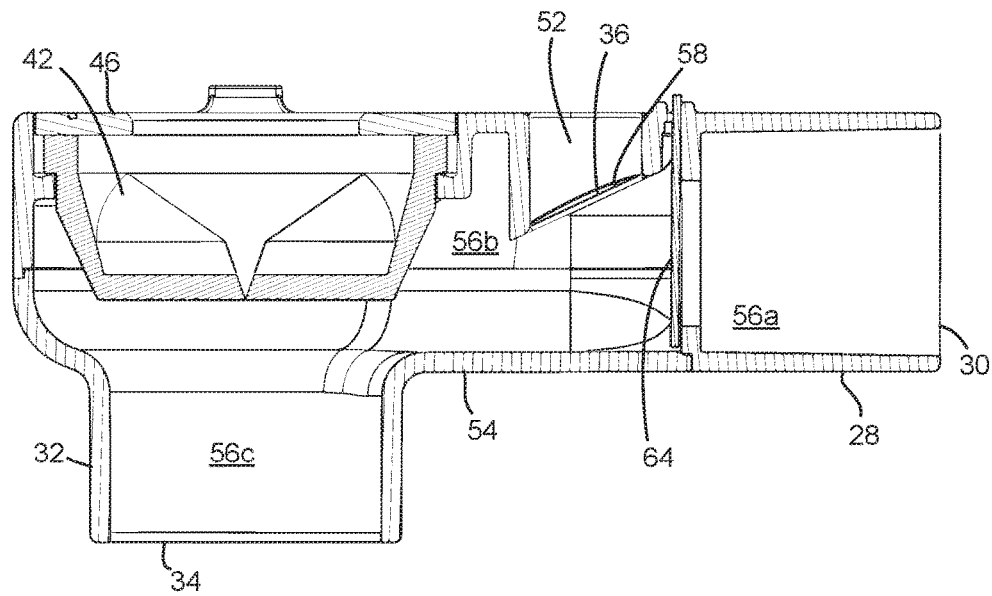
Fig. 2C
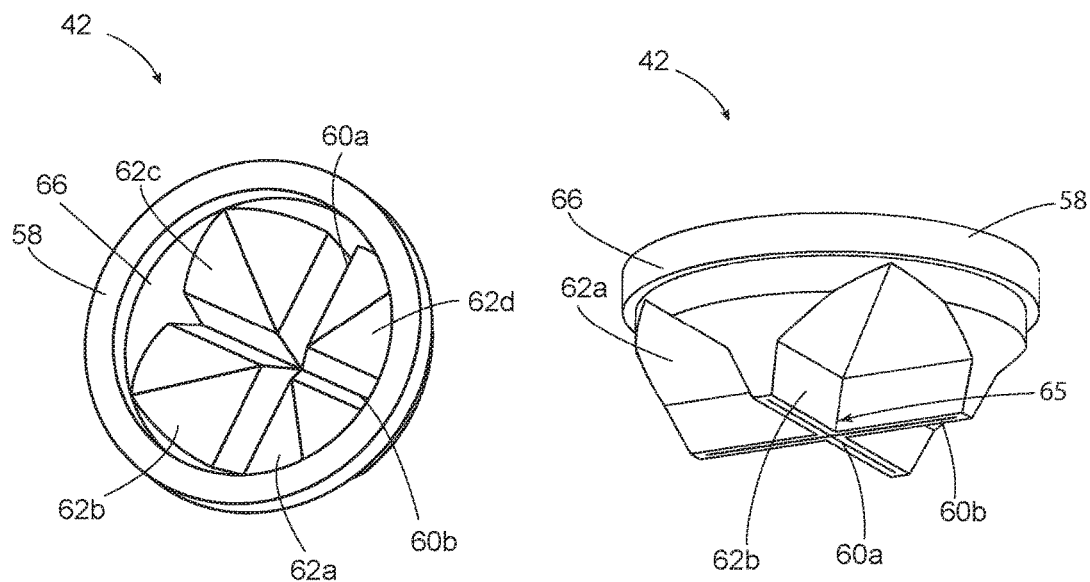
Fig. 3A
Fig. 3B

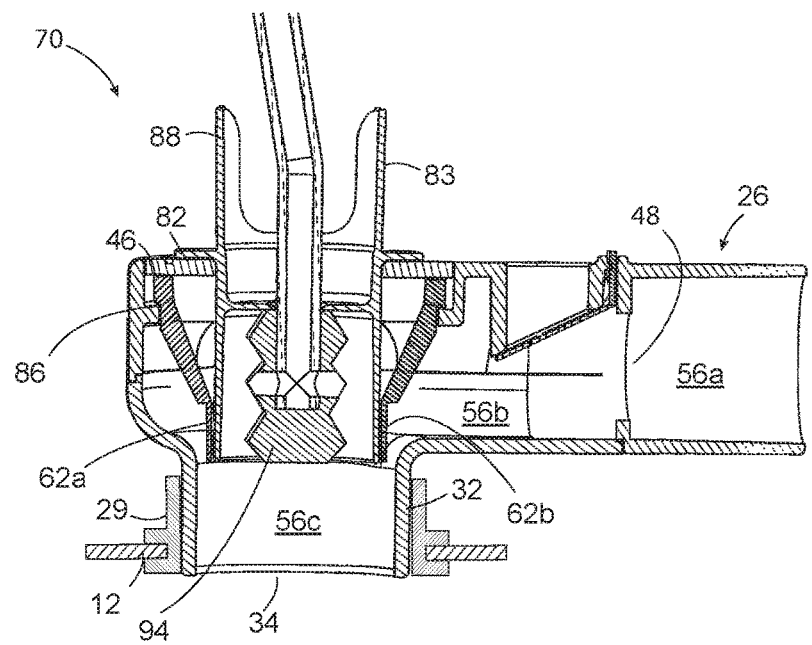
Fig. 9A
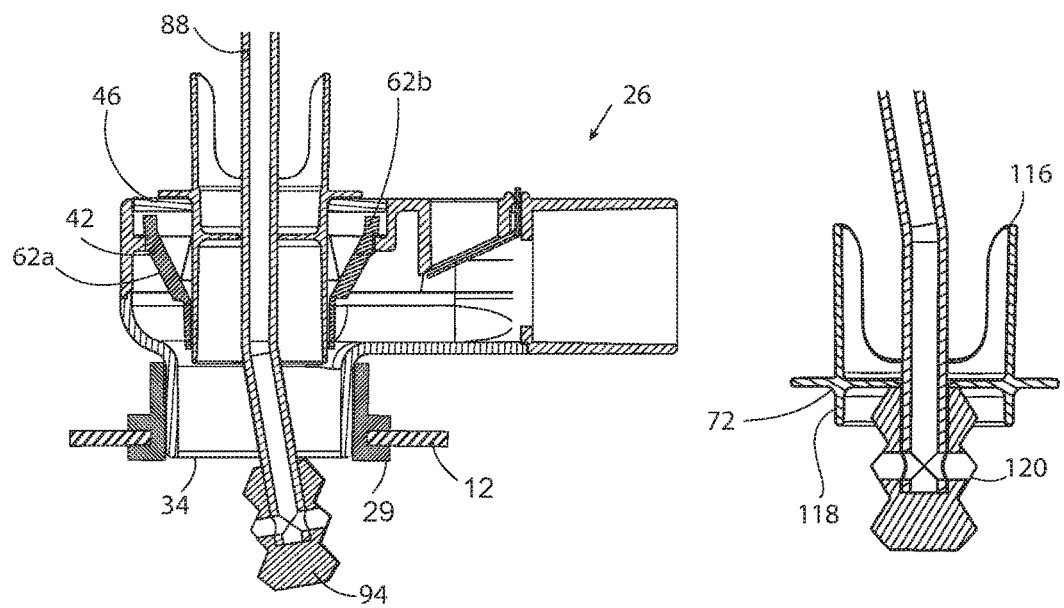
Fig. 9B
Fig. 10

POSITIVE PRESSURE VENTILATION APPLIANCE MODULES AND RELATED SYSTEMS AND METHODS

CROSS-REFERENCE TO RELATED APPLICATIONS

This application is a continuation of U.S. application Ser. No. 15/870,107, titled Positive Pressure Ventilation Elbow and Related Masks, Systems, and Methods, filed Jan. 12, 2018, which is a continuation in part of PCT Application No. PCT/US2016/039117, which claims the benefit of US Provisional Patent Application Nos. 62/183,733, filed Jun. 23, 2015 and 62/252,577 filed Nov. 8, 2015. Application Ser. No. 15/870,107 is also a continuation in part of PCT Application No. PCT/US2017/060480, which claims the benefit of U.S. Provisional Patent Applications Nos. 62/418,787, filed Nov. 7, 2016 and 62/568,314, filed Oct. 4, 2017. All of the foregoing applications are hereby incorporated herein by reference in their entirety.

BACKGROUND

1. Field of the Invention

The present invention relates to devices and method for providing respiratory care procedures through a non-invasive positive pressure mask.

2. Related Technology

Positive pressure ventilation (PPV) masks are currently used in the medical field for patients with poor oxygen saturation, sleep apnea, and other related respiratory problems. The mask includes a peripheral flexible membrane that contacts the face of the patient and creates a seal with the face using the positive pressure. An example of a positive pressure ventilation mask is disclosed in U.S. Pat. No. 6,513,526 to Kwok. These types of masks, used with a ventilator, can provide positive pressure airflow for critically ill patients without the need to intubate the patient and/or allow earlier extubation.

Positive pressure masks require an effective seal around the facial area and can be a hassle for clinicians or users to properly place. Once in place, the positive pressure in the mask assists the patient's breathing by providing a proper amount of forced air necessary to maintain adequate inhalation and exhalation. In a matter of hours or days, the mask can cause discomfort to the patient from dry mouth or nose, nasal congestion, rhinitis or runny nose, facial irritations, bloody noses, dry mucosal tissue, dry lips, increased risk of respiratory infection, or other difficulties managing oral or nasal airway.

Positive pressure masks are also used to treat sleep apnea. While these patients are typically not critically ill, they suffer from the inconvenience of dryness of the airway and the inability to access their oral airway without taking the mask off.

SUMMARY

The present invention relates to appliance modules, capnometry modules, nebulizer modules, oral care kits, ventilators and ventilator systems and methods of performing PPV procedures using the modules and systems. The devices and methods utilize an access port through the mask (either the mask shell or an elbow connected to the shell). The access port provides access to the oral or nasal cavity from outside the ventilator circuit without removing the mask.

Some embodiments of the invention relate to devices and methods that can be placed through the access port of the positive pressure ventilation mask. The devices include a PPV appliance adapter that has a first seal surface and a second seal surface to seal the appliance module to the access port and to seal the adapter to the appliance. The second seal surface defines an aperture that forms the second PPV seal with the appliance. The appliance adapter has two surfaces, one on the inside of the mask, which is exposed to the ventilator pressure and a second that is outside the mask and exposed to pressures external to the PPV mask when the adapter is attached.

In some embodiments, the appliance module includes an elongate tube positioned in the aperture of the adapter and a working head positioned on the elongate tube. The elongate tube and the aperture slide relative to one another while maintaining the second seal. The working head has a larger diameter than the aperture, which prevents the working head from being passed through the aperture. The working head is positioned on inside of the adapter such that the working head can be used in the oral or nasal cavity of the patient when the appliance module is inserted into the access port.

Examples of appliances that may be included in the appliance module according to the invention include, but are not limited to, a suction swab, a suction brush, a yankauer, a cannula, a swab applicator, a capnometry sampling device, a nebulizer device, and the like.

Some embodiments of the invention relate to PPV masks that have a valve positioned in the access port that seals under pressure from the ventilator. An adapter (e.g., an appliance adapter) is configured to seal with the access port and open the valve. When the adapter is removed from the access port, the valve seals under the positive pressure of the ventilator. The access port and self-sealing valve may be positioned in a shell of the PPV mask or in an elbow connector of the mask. The valve can have curvature and/or leaflets that are pushed together from pressure on the inside of the mask to seal the valve when the valve is not being used (i.e., free of an appliance). The valve can also be self-reverting. The valve can be made of an elastomeric material and mounted to the mask such that its movable members will revert back to a self-sealing position when inverted. The valves can be relatively large to allow for oral care appliances to be passed therethrough. In some embodiments, the valve opens to a diameter of at least 5, 10, 15, or 20 mm.

Another embodiment of the invention relates to a suction brush module. The suction brush module has a working head that includes a suction brush. The brush adapter of the module includes a receptacle configured to house the brush and an aperture centrally located at a proximal end of the receptacle. The suction brush includes a suction head with an elongate tubing connected to the head. The elongate tubing is centrally located on a proximal end of the such that the aperture of the adapter and the suction brush tubing align axially. In some embodiments, the longitudinal axis of the tubing connector is off center from the longitudinal axis of the brush head by less than 30%, 20%, 10%, or 5%.

Another embodiment relates to a covered yankauer. The yankauer has a yankauer adapter that seals with an access port of an PPV mask. The yankauer adapter also includes a receptacle for housing the yankauer in a covered position. The yankauer is movable between a covered position and an exposed position in which the yankauer is extended from the cover. The yankauer has a cover that attaches to the adapter and the yankauer tubing and is compressed when the yankauer is moved from the covered position to the extended position.

Another embodiment relates to an oral care kit that includes individually packaged appliances. Each package includes an appliance module. In some embodiments, the individual packages include a tray with at least two compartments, one of which houses an appliance module and the other an oral rinse solution. The tray is sealed with a packaging material around the first and second compartments and can be opened by pealing.

Another embodiment relates to a capnometry module that includes an adapter configured to attach to an access port of the PPV mask. The capnometry module includes a support housing that extends on the inside of the adapter into the mouth of a person wearing the PPV mask with the module attached. The support housing includes a sampling line with an inlet at the oral end of the support housing. The sampling line passes through the adapter to the outside portion of the adapter where it connects to a capnometry device capable of measuring $CO_2$ in the sampled air.

In another embodiment, the capnometry adapter has a support housing that moves between a covered position and an extended position for use. The support housing forms a second slidable seal with the adapter such that the PPV seal is maintained as the support housing is inserted into the mouth of a person wearing the PPV mask. The moveable support housing may also include a sheath for covering the support housing when it is in the covered position (i.e., the oral end is retracted into the receptacle).

Another embodiment relates to a nebulizer module with an adapter configured to form a seal with a PPV mask. The adapter includes a tubing on the inside that extends into an elbow or a shell of a mask. An oral end of the tubing delivers nebulized gas into the mask or mouth of a patient. The opposite end of the tubing abuts a vibrating element. The opposite side of the vibrating element is in contact with a fluid reservoir that holds the fluid to be nebulized. The nebulizer module can include a control module for driving the vibrating element, a power supply, and a user input device (e.g., a button) housed within the adapter. Or alternatively the module can be connected to a control unit via wire.

Another embodiment of the invention relates to a ventilator system that has a control module that receives pressure input from a ventilation circuit and detects a suction pressure signal indicative of changes in pressure caused by operation of a suction appliance in the PPV mask. The control module uses the detected suction pressure signal when generating an output signal for driving the pressure generating system that produces positive pressure for the ventilator circuit (e.g., the suction pressure signal is filtered out).

Another embodiment of the invention relates to a ventilator that displays a menu to a user for selecting an oral care setting. Upon receiving input (selecting the oral care setting) the ventilator adjusts at least one parameter of the ventilator (e.g., temporarily sets a target leak rate higher for trigger an alarm).

DESCRIPTION OF DRAWINGS

FIG. 2C is a cross section of the elbow of FIG. 2A;

FIG. 3A is top perspective view of the self-sealing valve of the elbow of FIG. 1;

FIG. 3B is a bottom perspective view of the valve of FIG. 3A;

FIG. 9A is a cross section of the elbow of FIG. 1 and the suction swab module of FIG. 6A in a covered position;

FIG. 9B is a cross section of the elbow and module of FIG. 9A with the suction swab partially extended into a shell of a mask;

FIG. 10 is an alternative embodiment of an adapter and appliance;

DETAILED DESCRIPTION

The present invention relates to positive pressure ventilation masks and devices that provide or connect to and seal with a port of a positive pressure mask. The devices allow access to the mouth of the patient while maintaining sufficient positive pressure for the mask to seal and/or for the ventilator to provide the intended ventilation. Embodiments of the invention relate to access ports for inserting tools, valves for sealing the access ports, adapters for mating with the access port and/or opening a valve in the access port, and instruments that can be housed within an adapter configured to connect with the access port. Embodiments of the invention also relate to various instruments that are specifically configured for insertion through an access port in an PPV mask using an adapter, including suction swabs, suction brushes, swabs, covered yankauers, capnometry devices, endoscopy devices, nebulizer modules, nebulizers, microphones, and the like.

Positive Pressure Ventilation Mask with Access Port

The present invention utilizes a positive pressure ventilation mask with an access port. The access port may be an opening with a removable cap or a valve that can be selectively opened to attach an adapter. The access port may be built into the shell (also referred to as the mask body) of a PPV mask or into a connector (e.g., elbow) of the PPV mask. The valve may be a slit valve or a valve that seals under the pressure of the ventilator (also referred to herein as a self-sealing valve). The valve may also be self-reverting (i.e., made of a material and having a configuration that will revert back to its original configuration when inverted by an object being pulled through the valve). The valve can be positioned in the mask body or in a valve adapter.

Figure 1A:
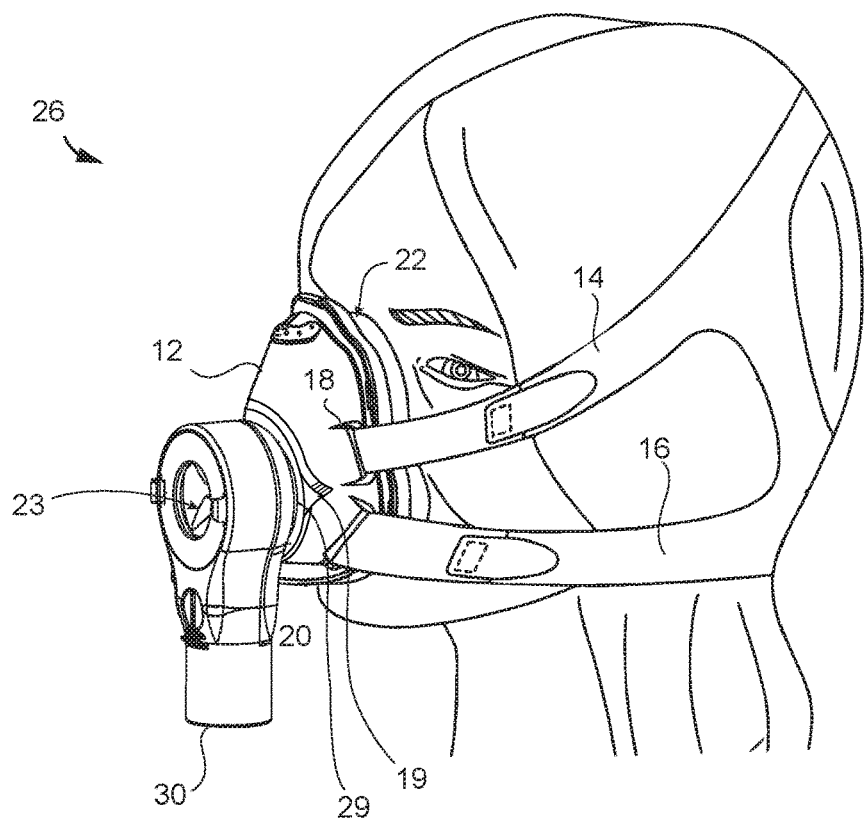
FIG. 1A illustrates a full face positive pressure mask, including an elbow having a valve that seals under ventilator pressure.
Figure 1B:
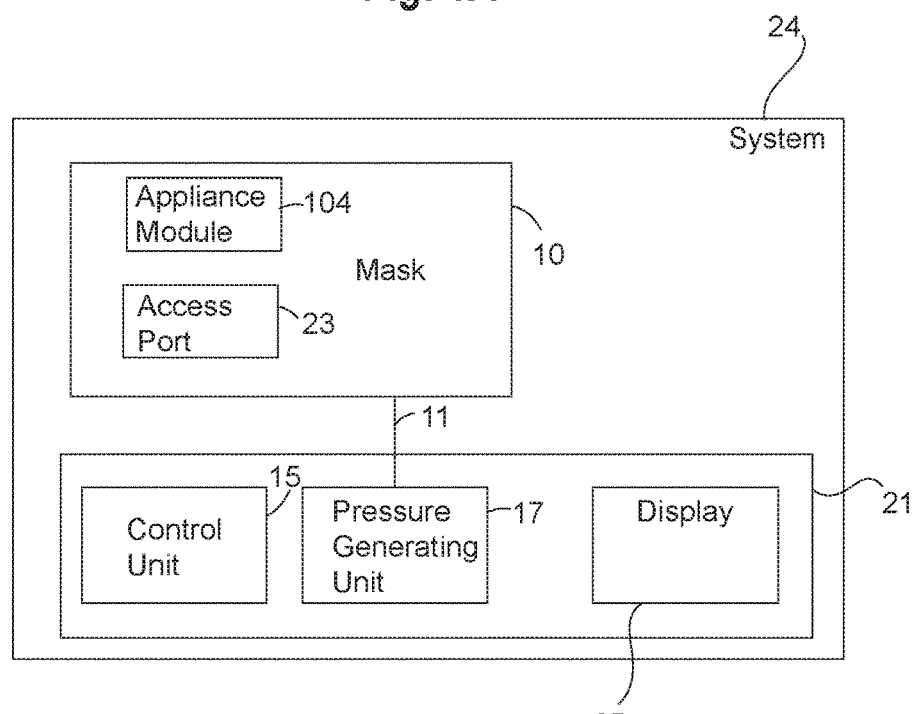
FIG. 1B illustrates a ventilator system including a PPV mask, ventilation circuit, and ventilator.

FIGS. 1A and 1B illustrate a positive pressure ventilation (PPV) mask 10 that includes a mask body 12 (also referred to herein as a "shell"). As shown in FIG. 1B, ventilator system 24 includes the mask 10, access port 23, and an appliance module including an adapter that connects to the access port 23. Ventilator system 24 also includes a ventilator unit 21 that connects to inlet 30 of the elbow 26 via a flexible hose (not shown) to form a ventilator circuit. The ventilator includes a pressure sensor that senses pressure in the system and is used by control unit 15 to control pressure by driving a pressure generating unit 17. Parameters of the ventilator can be displayed on display 25 and input received through a user interface (not shown). Ventilators used with the PPV masks of the invention are preferably bi-level pressure ventilators (or alternatively continuous pressure ventilators). Bi-level ventilation is typically important for critical care patients.

Mask body 12 may be a rigid or semi rigid material. Mask 10 can include headgear with headgear connectors adapted to be removably attached to the body 12. The headgear is used to secure mask 10 to the head of the patient using upper strap 14 and lower strap 16. Straps 14 and 16 connect to eyelets 18 and 20, respectively, on mask body 12. Straps 14 and 16 connect to eyelets on corresponding locations (not shown) on an opposite side of body 12. The straps secure the mask to the head, which allows a positive pressure seal to be obtained and also avoids movement of the mask relative to the head that could cause air leaks that diminish the positive air treatment.

At the periphery of the mask body 12, mask 10 includes a peripheral flexible cushion 22 that includes a thin flexible membrane (e.g., a flap) that can form a seal with the face of the patient when positive pressure is delivered from a ventilation system 24 through an elbow 26 and into an opening in mask body 12. The cushion can form a seal with the patient's face in a nasal bridge region, a cheek region and/or a lower lip/chin region of the patient's face. The mask body 12 defines a cavity (also referred to as a breathing chamber). The cushion may be constructed of one or more relatively soft, elastomeric materials connected to a frame (i.e., the shell) which is constructed of a second material that is more rigid than the cushion. The cavity of mask body 12 forms a positive air pressure chamber between it and the face of a person. For purposes of this invention the term "within the mask" means the chamber defined by the mask when on the face of a person. The masks are configured to be fluidly coupled to ventilator unit 21 through air supply connector 26, such as an elbow.

Masks having membranes suitable for sealing around the mouth and nose of a patient using positive pressure are described in U.S. Pat. No. 9,119,931 to D'Souza, U.S. Pat. No. 9,295,799 to McAuley; U.S. Pat. No. 6,513,526 to Kwok, and D464,728 to Paul, U.S. Pat. Nos. 6,792,943 and 8,365,734 to Lehman, and international application publication WO2017021836A1 to Rose, all of which are hereby incorporated herein by reference. The mask may also include an exchangeable two mask system such as the FDA cleared AF541 mask by Respironics (Murrysville Pa., USA) and masks with similar features and function.

Figure 2A:
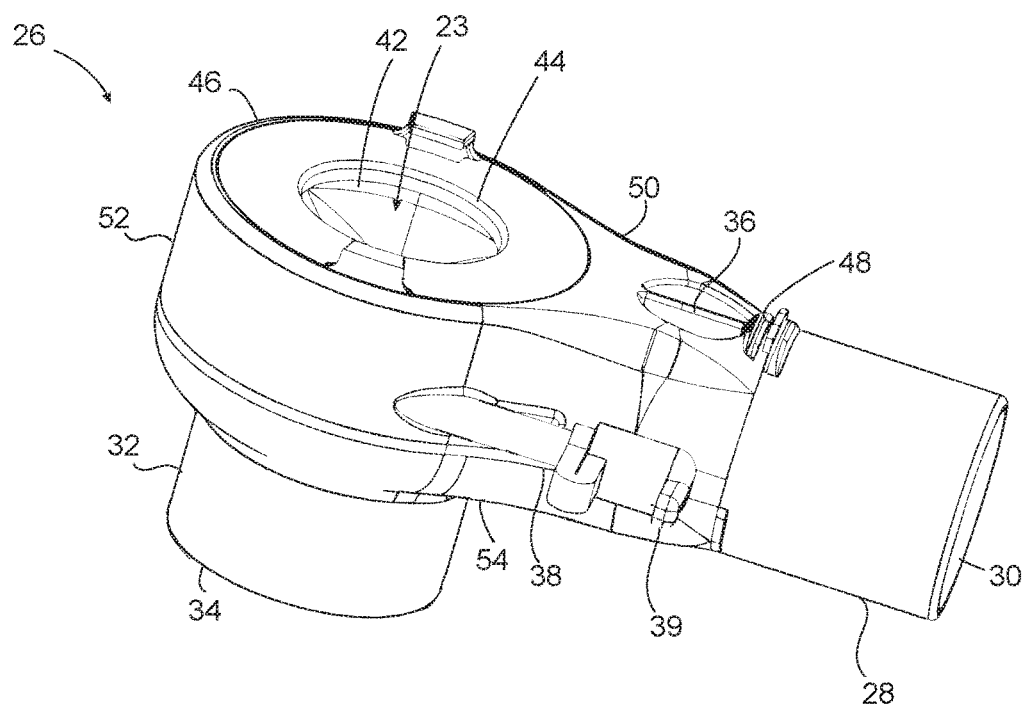
FIG. 2A is a perspective view of the elbow of FIG. 1A.
Figure 2B:
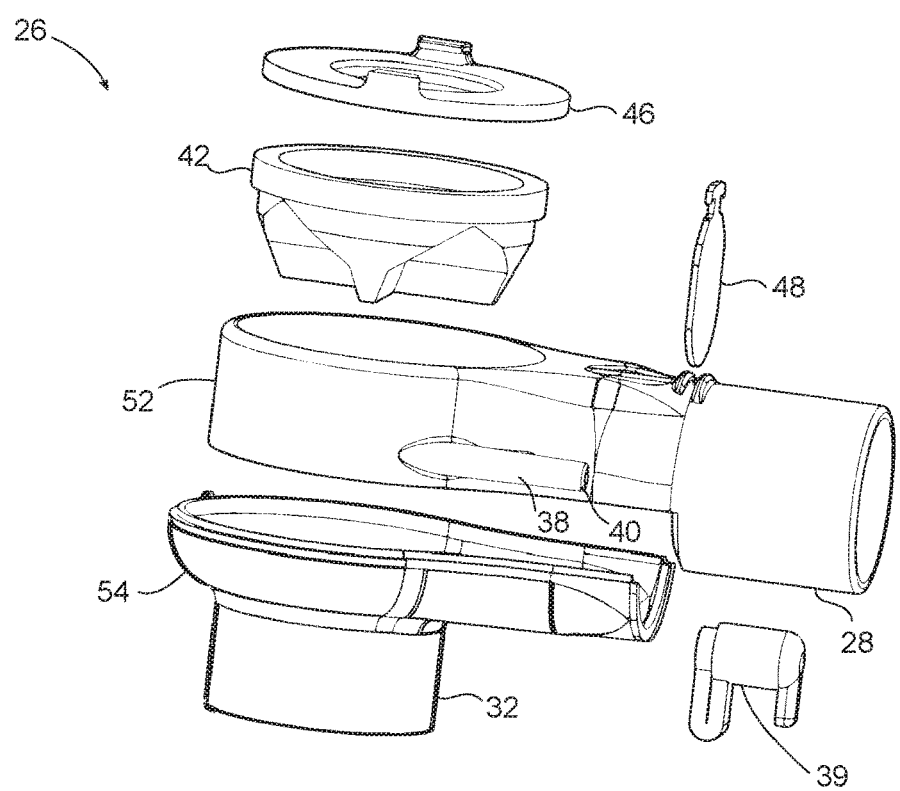
FIG. 2B is an exploded view of the elbow of FIG. 2A.

FIGS. 2A-2C show the elbow and valve in more detail. Elbow 26 includes an elbow body 50 formed from upper housing 52 and lower housing 54. An access valve, such as cross-slit valve 42 is secured to upper housing 52 using a locking ring 46. Elbow 26 also includes an anti-asphyxiation valve that uses a flap 48 to open and close aperture 36. For purposes of this invention, unless otherwise stated or implied, the term "valve" by itself refers to the "access valve" in the access port 23.

Elbow 26 is an air supply connector that includes an air-delivery conduit. The air supply conduit extends between inlet 30 and outlet 34 and includes internal regions 56a, 56b, and 56c (FIG. 2C). Valve 42 is in fluid communication with the air delivery conduit in region 56c. Valve 42 provides access to a wearer's mouth and nose through aperture 44 and region 56c of the conduit, thereby providing a port with direct access to the mouth of the patient.

The air supply conduit provided by elbow 26 is configured to deliver pressurized air from a source of positive air pressure (e.g., ventilator unit 21) to the cavity of the ventilation mask 10. Air pressure in inlet 30 forces flap valve 48 to open to provide fluid communication between regions 56*a* and 56*b*. The air flow between region 56*a* and 56*b* forces flap 48 upward to close off aperture 36 by seating against rim 58. If air flow stops between regions 56*a* and 56*b*, flap 48 drops down to opening 65 to prevent air from flowing backwards through inlet 30 (i.e., from region 56*a* to 56*b*). Flap 48 prevents asphyxiation by allowing air to be breathed from the ambient (through aperture 36) if the supply of air from the ventilator is interrupted.

Elbow 26 includes a first press-fit connector 28 that serves to fluidly connect a positive pressure air supply hose (not shown) to inlet 30 of elbow 26. A second press-fit connector 32 serves to fluidly connect the outlet 34 of elbow 26 to an inlet in mask body 12. The press-fit connection may be configured to be sufficiently tight that when an appliance is positioned in the adapter (see FIG. 9B) and pulled out of valve 42, the press fit maintains the connection of the air supply connector to the mask. FIG. 1 illustrates a mask with a swivel connector 29 configured on the body 12 of the mask. A press fit connector 32 is placed inside of the swivel connector 29 and is configured to be sufficiently tight to deliver air to the mask. The swivel connector has textured finger grips 19 that are used to press on the swivel or rotate the elbow 26.

Elbow 26 preferably swivels relative to mask body 12 such that a hose connected to an elbow 26 can be redirected without torqueing the mask. Any swivel mechanism can be used. The swivel mechanism may be incorporated into a mask body, elbow, or the connection there between.

Connections other than press-fit may be used to connect an elbow 26 to a mask or ventilation system, including non-removable connections, screw fit with screw threads, snap connection, slide in connection with securing ridges, clips, and quick release connections.

Figure 5:
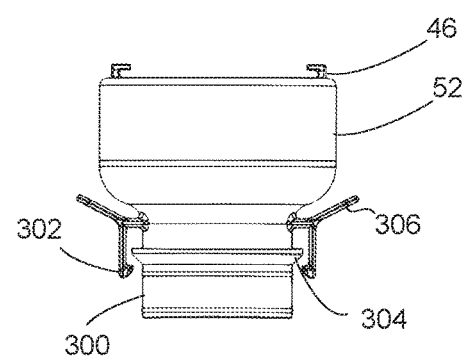
FIG. 5 illustrates an alternative embodiment of an elbow with a swivel connector.

FIG. 5 illustrates an embodiment wherein the elbow forms a swivel connection with the mask. A swivel connection portion 350 is shaped to fit in an opening of a PPV mask. The swivel connector 350 is also configured with a sealing rim 354 that will seal with the edges of an opening on the mask. The elbow includes clip connectors 352 that snap into a ridge or mount on the body of the mask to keep the elbow securely fit and sealed on in the access port. Release tabs 306 are attached to the clip connector that flex the clips 352 when pressed inward to release the elbow form the mask.

With reference again to FIGS. 2A-2C, elbow 26 may also include a pressure port 40 on stem 38. Pressure port 40 includes a small opening in fluid communication with region 56*b* that is used to monitor pressure changes in elbow 26. Changes in pressure can be used to detect when the wearer of the mask is inhaling or exhaling. Bi-level pressure ventilators can use the pressure port 40 to provide lower pressure during exhalation and increased pressure during inhalation. Pressure port 40 is not required to be associated with elbow 26, but rather can be placed in mask body 12, tubing between the ventilator and mask, or combinations of these. Pressure port 40 can be covered with a cap 39 to plug and stop flow when detection is not necessary.

Elbow 26 has an access port 23 with aperture 44 and a valve 42 positioned within the port. Valve 42 may be a self-sealing valve that uses pressure from the ventilator to close the valve when the access port is clear of an appliance or adapter. The access valve has an open diameter sufficient to perform oral care or insert an appliance therethrough with reduced leaking as compared to an access port without the valve and having the same maximum diameter opening. The diameter of the opening in the self-sealing valve (in the fully open position) can be at least 5, 10, 15, or 20 mm (~0.2, 0.04, 0.06, 0.08 in) and/or less than 50, 40, 30, 25, or 20 mm (~2, 0.16, 0.12, 0.1, 0.08 in) and/or within a range of the foregoing (in the height and/or width of the opening based on a cross section of the opening). These diameters of opening can be achieved with a valve that will be self-sealing under pressures of at least 4, 5, 8, or 10 cm $H_2O$ and/or less than 30, 25, 20, 15 cm $H_2O$, or within a range of any of the foregoing endpoints.

In some embodiments, the opening in access valve 42 is provided by one or more slits. The length of the slit may provide the maximum open width. In some embodiments, the valve includes a plurality of slits. In some embodiments, the valve can include two slits and the slits may form a cross-slit.

To facilitate self-sealing under pressure, access valve 42 may have inward sloping walls or concavity that the pressure pushes against. Valve 42 may be a duck bill valve or a dome shaped valve. FIGS. 3A and 3B illustrate a duckbill valve with a cross-slit. Valve 42 has a rim 58, support wall 66, and a plurality of leaflets 62*a-d*. As seen in the top view of FIG. 3A the leaflets are each concave relative to the ventilator pressure side of the valve and form fenestrations at slits 60*a* and 60*b*. The leaflets 62 are configured to be pushed open by an appliance or appliance adapter from an outside side of the valve and pushed together by pressure from the inside side of the valve. The duck bill valve is shown with 4 leaflets, but may have a single leaflet (i.e., seals against a rigid wall) but more preferably has at least 2, 3, 4, or more leaflets. As shown in FIG. 3B the concavity of leaflets 62 have a geometry that meets near the center of the cross slit. For example, the concavity of leaflet 62*b* meets near point 64. When an appliance or adapter is inserted the leaflet 62*b* is forced out and point 64 moves away from the center cross, thereby opening the valve. Valve 42 can be made from an elastomeric material with shape memory such that upon removing the appliance or adapter, the device recovers at least a portion of its concavity such that the pressure can seal the leaflets.

Where a dome valve is used, the dome may have a tapered thickness that is thin at a center opening and tapers to a greater thickness towards the edges. The taper may include a change of thickness greater than 1.2, 1.5, or 2 times the thickness at a lateral edge of a fenestration/slits as compared to a center edge of a fenestration. The taper may allow the valve to open more easily at the center.

In a preferred embodiment, the valve reverts itself if it becomes inverted (i.e., self-reverting). For purposes of this invention, a self-reverting valve has a material and configuration that causes the valve to return to its self-sealing position when inverted (e.g., an elastomeric material with shape memory). Thus, if an instrument is pulled out of the valve and a leaflet or other component is inverted, the self-reverting valve returns to its self-sealing position once the force is removed. Although not required, the valve may be concave and/or made of a silicone material (or similar polymers, elastomers, isoprene, Nitrile rubber, Butyl rubber, or silicone like material) to facilitate self-reverting. In one embodiment, the valve includes a layer of material at its center that is less than 5, 4, 3, or 2 mm thick.

The access valve 42 and/or combination of one or more of the access valve 42, anti-asphyxiation valve 42, and mask 10 may be configured to have a leak rate less than 70, 50, 40, 30, or 25 liters per minute ("lpm") and/or greater than 2, 5, 7, or 10 lpm and/or within a range of the foregoing when the mask is under an air pressure of at least 5, 10, 15, cm $H_2O$ and/or less than 25, 20, or 15 cm $H_2O$ or within a range of the foregoing. For purposes of this invention, the leak rate is measured at a pressure of 5 cm $H_2O$ when measured in accordance with ISO standard 17510 (2015).

In some embodiments, the valve may include a biocompatible lubricant to facilitate insertion of appliances or appliance adapter through the valve. The access valve and/or lubricant may also include an anti-microbial agent (e.g., chlorhexidine). In some embodiments, the valve adapter may have a dust cap that covers the opening to valve 42 the valve is not in use.

Figure 4A:
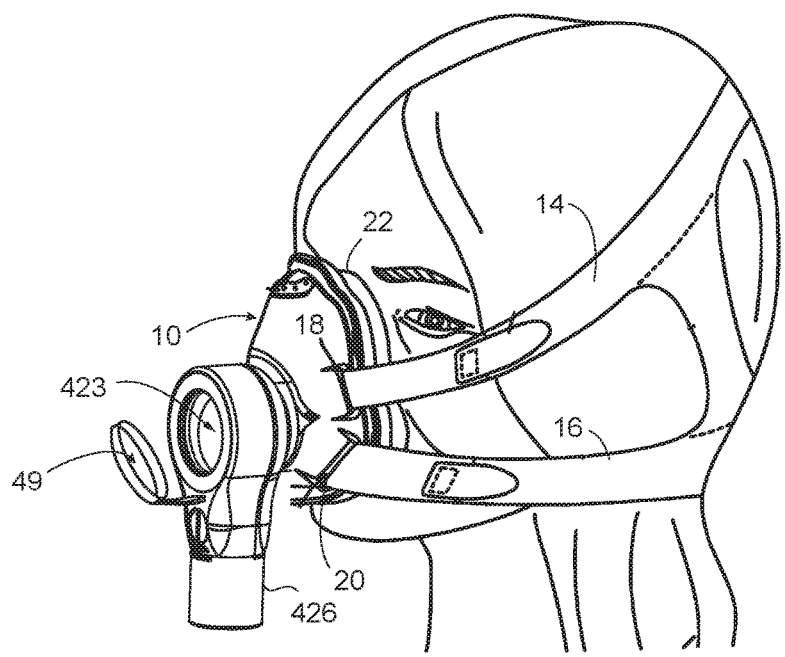
FIG. 4A illustrates an alternative embodiment of a full face positive pressure mask, including an elbow a port having a cap and no value.

FIG. 4A shows an alternative embodiment with an elbow 426 that does not include the access valve 42 of elbow 26 from FIG. 1. Elbow 426 includes an aperture 44 configured to receive appliance adapters that will seal the aperture 44 when the adapter is attached and/or placed through the aperture 44 (see FIGS. 7A-C). Because access port 23 of elbow 426 does not have a valve that seals the port when not in use, elbow 426 includes a seal cap 49 that can be placed over or in aperture 44 to prevent air leakage and to maintain air pressure between the mask and the face.

Figure 4B:
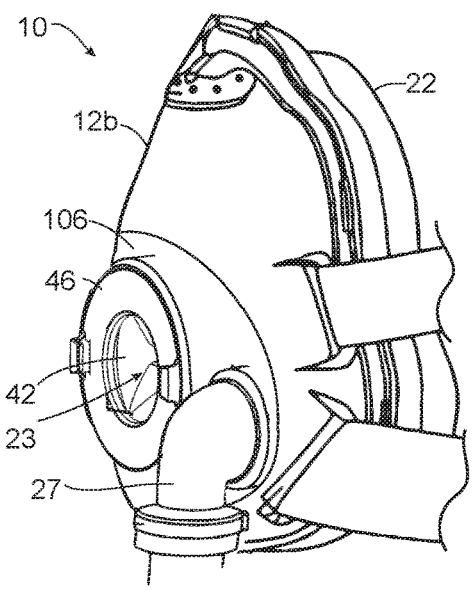
FIG. 4B illustrates an alternative embodiment of a full face positive pressure mask with an access port.

FIG. 4B illustrates an alternative embodiment of a mask 10 having a shell 12b that incorporates the access port 23 into the shell 12b instead of the elbow connector. Shell 12b has an elbow connector 27 separate from access port 23. Elbow connector 27 supplies pressurized air to the mask and may have any features known in the art for elbow connectors used on PPV masks. Similar to mask 10 of FIG. 1, valve 42 seals access port 23 using positive pressure in mask 10. Placing access port 23 in the mask separate from the elbow connector allows elbow 27 to be smaller than elbow 26 of FIG. 1.

The access port in shell 12b may also be configured without a valve as shown in access port 423 of FIG. 4A. In addition, access ports 23 (with or without a valve) can be placed anywhere on shell 12b that allows direct external access to the mouth or nose of the patient (i.e., access to the mouth or nose through the mask).

FIG. 4B also illustrates one embodiment showing a mask body 12b with a flexible portion 106 that is more flexible than the material of the adjacent portion of mask body 12b. The flexible portion 106 provides greater articulation and movement for appliance adapters placed through the access valve 42 as well as support and flexibility in maintaining a seal around the face created by the cushion 22. The flexible portion 106 of shell 12b can also be incorporated into mask body 12A of the embodiments shown in FIGS. 1A and 4A. In an alternative embodiment, the swivel connector 29 of FIG. 1A or 4A can be configured to be more flexible than the body of the mask 10. Flexible elbow connectors are further described in U.S. Pat. No. 8,302,605 which is hereby incorporated herein by reference. In yet another embodiment, the access port may be an iris valve such as the valve described in US2003/047189 to Kumar, which is hereby incorporated by reference.

Appliances, Adapters, Modules, and Kits that Maintain Positive Pressure

Some embodiments of the invention relate to appliances (e.g., scrub brushes, suction devices, $CO_2$ sampling lines, nebulizers, microphones, yankauers, and bite blocks) that include an appliance adapter. The appliance adapter can be coupled with an appliance to form an appliance module. The appliance adapter allows an appliance to pass through an access port on a PPV mask while maintaining pressure inside the mask. For instance, a suction swab appliance can be coupled with an appliance adapter to form a suction swab module (see FIG. 6A) that can be inserted into the access valve 42 and then used to perform oral care on a patient while maintaining positive pressure in the mask. (as illustrated in FIG. 9B)

The appliance adapter is preferably configured to work with an access port, preferably one that includes an access valve that seals under pressure from the ventilator (e.g., the self-sealing and self-reverting access valves as described herein) and is configured to engage the appliance adapter to seal off the access valve. The appliance coupled with an appliance adapter can include but not limited to a suction brush, toothbrush, suction tube, $CO_2$ sampling lines, nebulizers, microphones, endoscopy devices to form a variety of appliance modules. Providing a variety of appliance modules to a patient using one mask with an access port or access value can be important because it may not be known which particular procedures need to be performed on a patient when the mask is placed. Providing an access port or valve on a mask that can receive a number of different appliances for different procedures will allow patients to receive the desired care or procedures necessary for their conditions. This can be done without having to remove or exchange masks or elbows, especially when removing a PPV mask or elbow is clinically undesirable.

Appliance Adapter

Sealing structures on the appliance adapter provides a sealing surfaces that engage with and seal the adapter to both of an access port in a PPV mask and a portion of an appliance. The sealing structure may be a wall, rib, chamfered seat, membrane, gasket or other structures suitable for performing the function of sealing adapter to an access port or appliance.

Figure 7A:
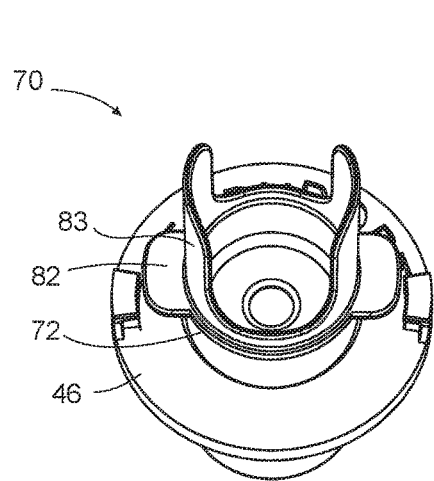
FIG. 7A-C illustrate the ring of the elbow of FIG. 3A and the adapter of the module of FIG. 6A in various positions relative to one another.
Figure 7B:
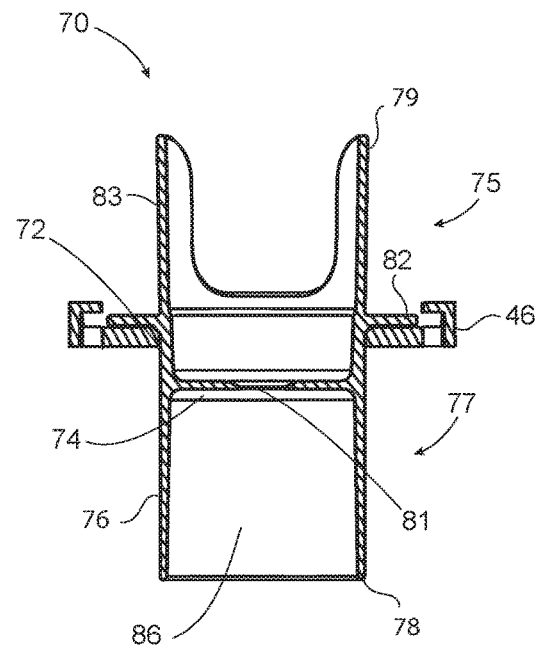
Figure 7C:
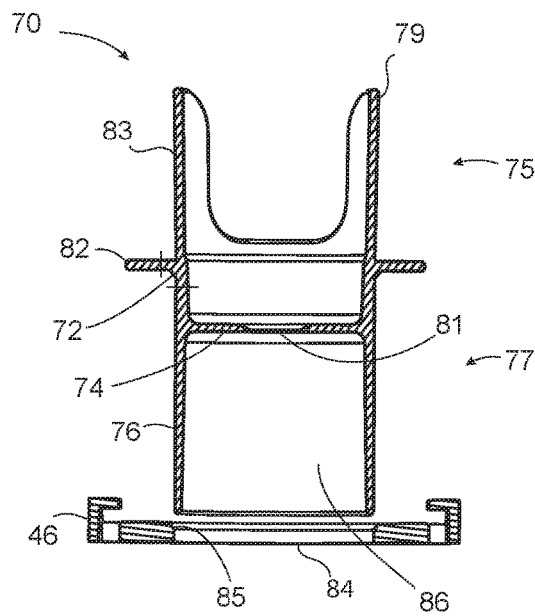

In one embodiment, as show in FIG. 7A-7C, the appliance adapter includes a housing 76 (also referred to herein as "body") that extends from an oral end 78 to a proximal end 79. The housing includes a seal surface 72 (on the periphery thereof) and a housing member 74 on an interior of housing 76 that divides the adapter into, an outside portion 75, and an inside portion 77. Inside portion 77 extends from the seal surface 72 and housing member 74 toward oral end 87. Inside portion includes the surfaces that are on a side of the adapter that is exposed to the pressure of the ventilator when the adapter is attached to the access port. The outside portion extends from sealing surface 72 and housing member 74 toward proximal end 79. The outside portion of the adapter includes those surfaces that are exposed to pressures external to the mask (i.e., ambient pressures).

The sealing surface 72 is configured to form a PPV seal with an access port (e.g., access port 23) when attached to PPV mask 10. FIGS. 7A-7C show the engagement of the ring structure of elbow 26 with the remainder of the access port removed for clarity. FIG. 7A shows ring 46 with adapter partially inserted. FIG. 7B shows adapter 70 fully seated and sealed with ring 46. FIG. 7C shows adapter 70 completely removed from ring 46.

As best seen by a comparison of FIGS. 7B and 7C, when ring 46 and adapter 70 are fully seated or engaged, seal surface 72 engages a wall 84 and chamfered structure 85 of ring 46. The seal is formed from the tolerance of the diameter of the wall 84 and the surface of the tubular housing 76 forming sealing surface 72. The seal may be a slidable seal where the seal is formed on a tubular structure that slides through aperture 44.

In some embodiments, the seal surface 72 may be a chamfered structure that mates with chamfered structure 85 of the ring. The chamfer may be formed in a rib with a diameter of less than 0.1 or 0.05 inch. The length of the adapter as measured from the seal structure to an oral end of the adapter is at least 0.3, 0.6, 1.2, 2.4, or 5 inches and/or less than 8, 6, 4, 2, 1.5, 1, 0.6, or 0.3 inch and/or within a range of any of the foregoing endpoints. The PPV seal may be formed between surfaces of the adapter and access port having a gap less than 0.02, 0.015, 0.01, 0.006, or 0.003 and at or greater than 0.0, 0.001, 0.002, 0.003, 0.005, 0.006, 0.01 inch or within a range of the foregoing endpoints. The inside portion of the adapter may have a maximum or minimum outer diameter less than 3, 2, 1.5, 1.2, or 0.6 inch and/or greater than 0.3, 0.6, 0.8, 1.0, 1.5 inch and/or within a range of the foregoing endpoints. Selecting a proper gap can be important for making it easy to remove the adapter from the access port, especially when the access port has a valve in it. In some embodiments, the adapter can form a PPV seal and the adapter can be removed by pulling on an appliance to slide the adapter out without gripping the adapter.

Adapter 70 also includes an appliance aperture through which an elongate member (e.g., a tube) of an appliance can slidably seal. The housing member 74 may define the appliance aperture for receiving the elongate member of the appliance. The adapter aperture 81 is configured to seal with a portion of the appliance.

The appliance aperture may be a septum in a tube. The housing member may be injection molded with a housing wall of the adapter, which avoids the need for assembling a separate structure to form the seal. Applicant has surprisingly found that an injection molded housing member with a small aperture can form a sufficient PPV seal and allow sliding and articulation of a tube. To ensure sufficient articulation of the elongate member, the housing member adjacent the appliance aperture should be thin. The housing member forming the aperture and engaging the elongate member may have a maximum and/or minimum thickness less than 0.5, 0.1, 0.05, 0.01 inch and/or greater than 0.005, 0.01, 0.02, or 0.04 and/or within a range of any of the foregoing endpoints.

Adapter 70 may include a receptacle 86 formed on the inside portion of the adapter. The receptacle may provide a cover for a working head and/or may provide space for articulating a shaft of an appliance from side to side with the working head inserted. Receptacle 86 may define a cavity with dimensions as described above with regard to the inside portion of the adapter. The appliance can provide protection to an appliance when being inserted through a valve. For example, when coupling the appliance adapter to a mask with a self-sealing valve, the appliance adapter may have a receptacle for housing a compressible material, such as a sponge. The receptacle can prevent the sponge from being squeezed by the valve when retracting the suction swab module from the access valve. The receptacle may provide access through the self-sealing valve without compressing the material. (see FIGS. 9A and 9B)

While the invention has been illustrated with a housing member that is integral to the adapter body, it will be appreciated that other sealing features can be used, including the sealing features described above with regard to the first seal. In one embodiment, the appliance adapter may have a flexible membrane sized and configured to seal around a portion of an appliance. The flexible membrane allows the appliance to be manipulated through a port by flexing the membrane.

The user of the device can place the application module into the access port or access valve 42 by gripping the vertical grip tab 83 on the outside portion 75 of the adapter 70. The receptacle 86 of the adapter 70 is placed through the aperture 44 of the locking ring 46 and passes into the access valve 42. (as shown in FIG. 9A) As the receptacle 86 slides through the lock ring aperture 44 the horizontal tabs 82 contact against the surface of the locking ring 46 as shown in FIG. 7B. This contact will form a temporary fixed platform for stability while providing oral care or other procedures are performed through the PPV mask. This surface contact will also provide a tactical and visual connection and will provide feedback to the user that the adapter is properly placed.

Figure 8:
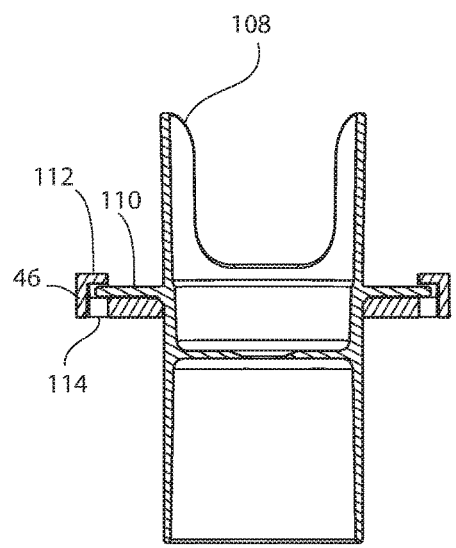
FIG. 8 illustrates an alternative embodiment of the adapter and ring of FIG. 7B in which the adapter locks to the ring.

The appliance adapters of the present invention may also include a locking feature to releasable lock to ring 46. Any lock feature may be used, including bayonet, snap connect, press fit, etc. The lock secures the appliance adapter to the valve adapter. The locking mechanism may include male and female components on respective locking ring and appliance adapter. FIG. 8 shows an adapter 108 with tabs 110 (male component) that extend laterally under lock feature 112 (female component) of ring 46 to form a bayonet lock. Male component (tabs 110) may also include a bump feature to engage a corresponding feature in lock feature 112 when lock feature is fully engaged (e.g., by twisting the tabs into the slot. A bayonet locking mechanism is desirable because the user can still insert the appliance adapter into the valve adapter without engaging the locking mechanism, if so desired. The locking mechanism is then easily disengaged by twisting. The bayonet mechanism also has the rotational mechanism transverse to the positive pressure forces acting on the membrane, which avoids the pressure causing the locking mechanism to fail.

FIG. 8 also illustrates a lock ring that can be molded with a straight pull to mold undercuts required for lock features 134. For example, ring 46 includes holes 114.

FIGS. 9A and 9B show a suction sponge module passing through the locking ring 46 and into the access valve 42. As the receptacle 86 passes through the access valve 42 it forces slits 60 open and leaflets 62 (e.g., 62a and 62c) to flex and create an opening in valve 42 that accommodates the receptacle 86, and thus the sponge 94 portion housed therein. Receptacle 86 forms the insertion portion of appliance adapter 70.

The receptacle 86 has an open end opposite the appliance surface of member 74 and the adapter aperture 81. The open end is configured to allow the sponge 94 or brush portion (e.g., or other portions of varies appliances) of the appliance to freely pass there through. The open end of the receptacle 86 may have a diameter in a range from 5, 10, 15, or 20 mm and/or less than 40, 35, 30, 25, 20, or 15 mm and/or within a range of any of the foregoing. The receptacle 86 may also extend beyond the leaflets of valve 42 when fully inserted. FIGS. 9A and 9B also illustrate swivel connector 29 and shell 12 of mask 10. As shown in FIG. 9B, working head (sponge 94) is inserted within the mask 10 by inserting it distally (i.e., toward the oral cavity) past shell 12. Further movement of the appliance places the brush portion (sponge 94) inside the oral cavity of the person wearing mask 10 with the adapter attached thereto.

While some embodiments of the invention utilize a receptacle, some adapters of the invention do not require a receptacle. For instance, appliance modules that mate with access ports that do not have a valve (e.g., FIG. 4A) may not benefit from a receptacle in some cases. FIG. 10 illustrates an adapter 130 that lacks a receptacle substantially covering the appliance head 139. Housing 140 provides a seal surface but does not extend towards the oral end enough to provide protection for head 139.

Oral Care Appliances and Modules

Figure 6A:
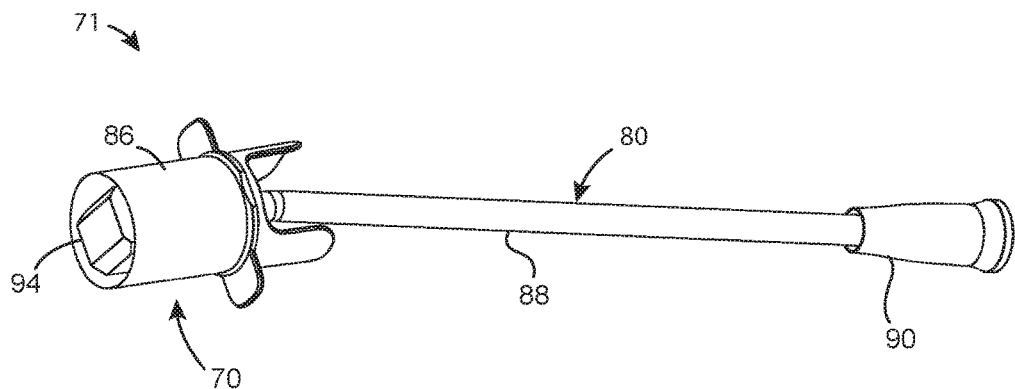
FIG. 6A illustrates a suction swab placed in an adapter in a covered position.
Figure 6B:
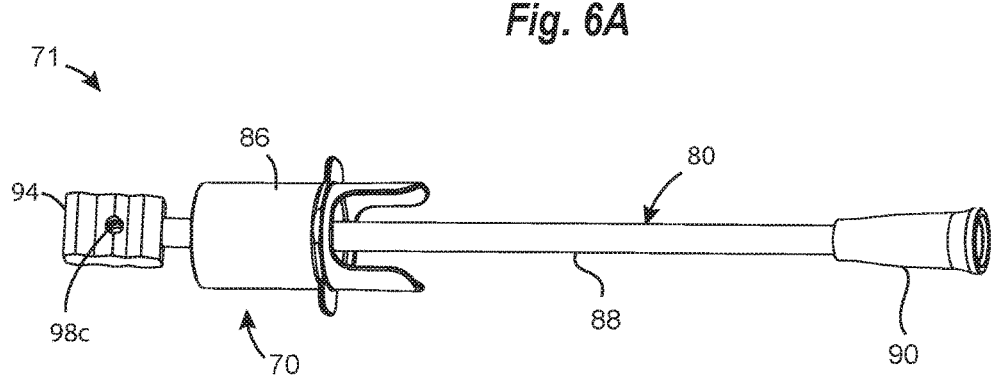
FIG. 6B shows the suction swab of FIG. 6A in a partially extended position.
Figure 6C:
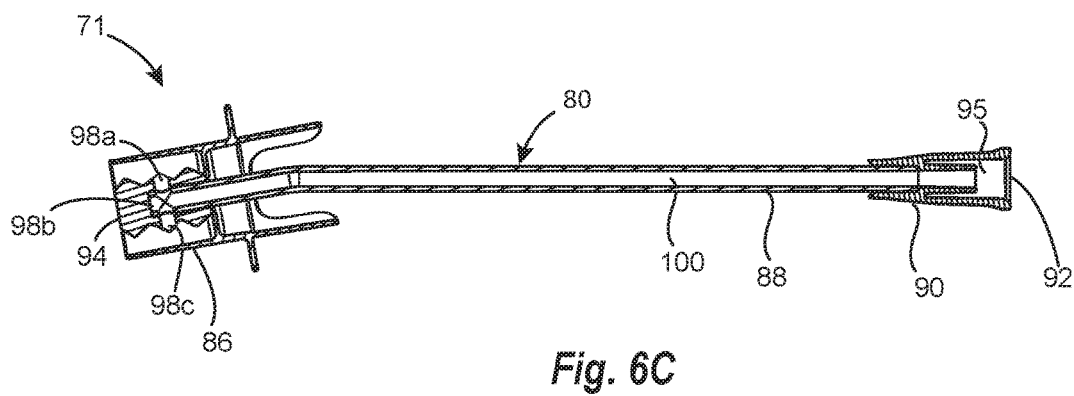
FIG. 6C is a cross section of the suction swab as in FIG. 6A.

FIGS. 6A-6C illustrate an example of a suction swab module 71 assembled with an oral care suction swab and an appliance adapter 70. The suction swab includes a shaft 88, a handle connector 90, and a scrub portion (sponge 94).

Shaft 88 has a suction channel 100 that extends from suction aperture 98a-c to outlet 92. The fluid pathway between suction apertures 98 and outlet 92 is in fluid communication with the handle connector 90 and handle connector port 95. Suction through apertures 98 can be carried out by attaching connector 90 to a suction handle (FIG. 11A) that is connected to a suction source.

In some embodiments, the appliance has a shaft that is longer than a corresponding traditional appliance to accommodate for the additional distance added by the depth of the mask, access port, and/or adapter.

With reference to FIG. 9A, in use, valve adapter 70 is in fluid communication with mask body 12 at region 56c and in fluid communication with a positive air supply from a ventilator at inlet 30 and flap valve 48 moves upward to open the conduit between inlet 30 and outlet 34.

Scrub brush appliance 80 (also referred to herein as suction brush 80) can be advanced into the mouth of a patient through region 56c of valve adapter 70 while member 74 creates a seal around shaft 88 of suction brush 80. Because receptacle 86 does not fully occlude the space in region 56c, airflow and thus positive pressure can continue to pressurize the chamber between the mask and the face of the patient. Fluids can be delivered to the mouth in sponge 94 and suction can be used to remove the fluids from the mouth through suction brush 80. Suction brush 80 can be manipulated in different directions, while still keeping a relatively good seal.

To remove sponge 94, scrub brush 80 is retracted until sponge 94 is again housed within receptacle 86. Valve adapter 70 is removed from valve 42 and valve 42 self-seals from the positive air pressure within region 56c pushing against leaflets 62 of valve 42, thereby causing slits 60 to close. If the user does not fully retract sponge 94 into receptacle 86 and the sponge catches on leaflets 62 and caused the valve to invert, the configuration of the leaflets 62 and the resilient material cause it to revert itself (i.e., self-reverting) under pressures described herein for positive pressure ventilation.

Oral Care Suction Handle

Figure 11A:
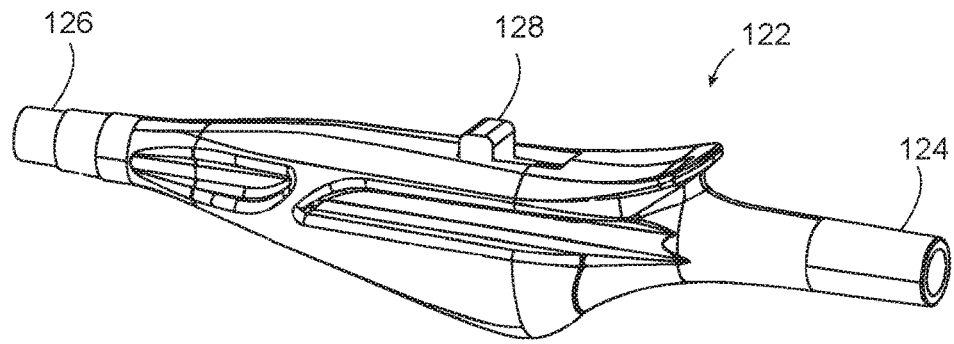
FIG. 11A shows a suction handle that includes a slider on/off switch.
Figure 11B:
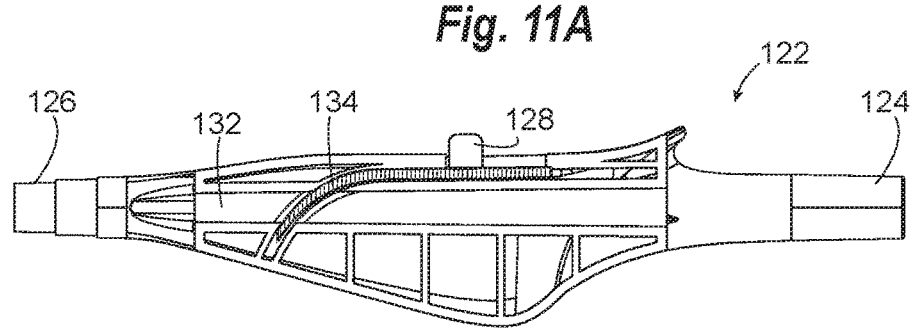
FIG. 11B is a cross section of the suction handle of FIG. 11A in the closed position.
Figure 11C:
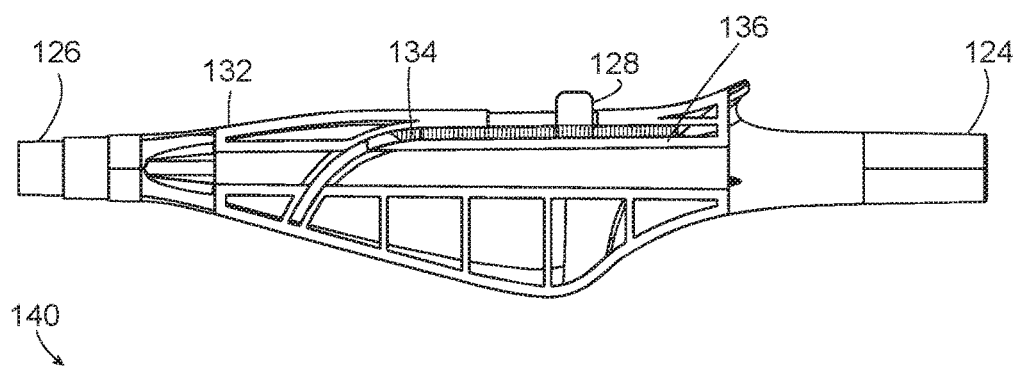
FIG. 11C is a cross section of the suction handle of FIG. 11A in the open position.

FIGS. 11A-C illustrate an example embodiment of a suction handle 122 configured for use with a suction appliance 104 such as suction brush 80. Suction handle 122 includes an appliance connector 124 on a distal end of handle 122 and a suction connector 126 on a proximal end of handle 122. A fluid channel 132 extends between connectors 124 and 126 for delivering fluids towards suction connector 126. Slider button 128 is movable between two positions (shown closed in FIG. 11B and open in FIG. 11C). A flap 134 extends across channel 132 in the closed position (FIG. 11B). In the open position, the slider is moved forward and flap 134 is no longer across the channel, thereby providing an open conduit for suctioning fluids. Another embodiment of the invention relates to an appliance handle that include both an on-off switch and a suction port (e.g., thumb port) (not shown). FIG. 11C shows the position 136, where a channel normal to channel 132 can be formed to place a suction port in housing 144 in front of slider button 128. The on-off switch allows the suction to be turned off when the device is not in use, but connected to a source of suctioning. The suction port allows the user to toggle the suction on and off during use by covering and uncovering the port. Suction to the patient is off by default when the port is not covered by a finger or other object. The default off position is created by the shorter path length to the suction port compared to suctioning through connector 126. When the suction port is occluded by a finger or other object, suction is transferred to the connector 126.

Suction Brush Module

Some embodiments of the invention relate to a suction brush module 140. Module 140 includes a brush appliance 142 that includes an elongate member in the form of an extruded tube 143. Tube 143 is connected on a proximal end to suction connector 146 and at a distal end (i.e., oral end) to a brush head 148. The brush head 148 is housed in an adapter 144 configured to connect to and form a seal with port 23 of mask 10 (FIG. 1A).

Tubing 143 includes a bend 145 that allows for greater articulation when the brush head is inserted into the mouth of a patient wearing mask 10 with module 140 attached thereto. Tube 143 may have a constant outer diameter to facilitate sealing between the tube 143 and an aperture of adapter 144 as described above. Brush head 148 is housed in a receptacle of adapter 144 and is slidably connected to adapter 144 in the same fashion as suction swab module described above (FIGS. 6A-6C and 9A-9B).

Figure 12A:
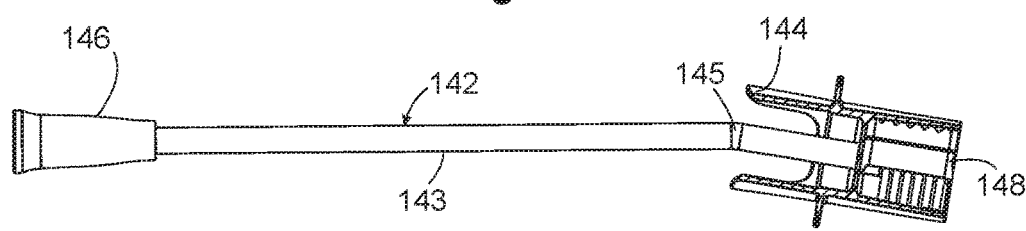
FIG. 12A illustrates a suction brush module.
Figure 12B:
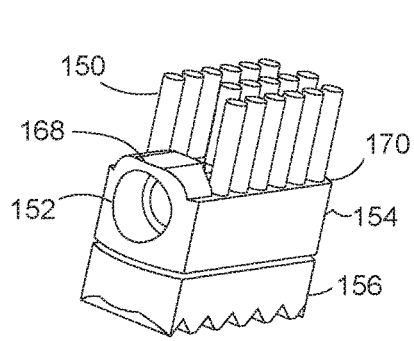
FIG. 12B is a perspective view of the brush head of FIG. 12A.
Figure 12C:
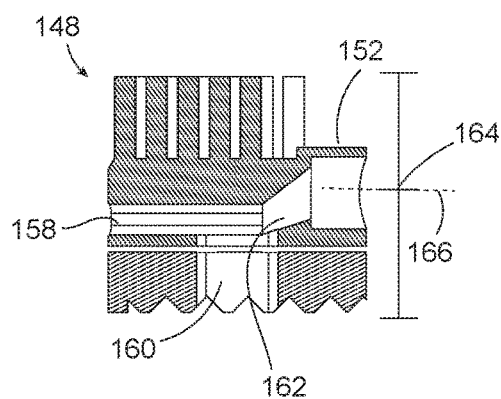
FIG. 12C is a cross section of the brush head of FIG. 12A.

FIGS. 12B and 12C illustrate brush head 148 in more detail. Brush head 148 has a plurality of bristles closely spaced on a surface 170 of head body 154. Bristles can be of the type placed in head 148 or alternatively can be a single injection molded part with head 148. Methods for injection molding bristles is disclosed in US20090007357 to Meadows, which is hereby incorporated by reference in its entirety. A sponge is attached to head body 154 opposite bristles 150. A tubing connector 152 is formed into head 148 for connecting tubing 143. Tubing 143 can be press fitted, glued, solvent bonded, or connected using any suitable joining method. Connector 152 has an upper portion 168 that is raised above surface 170 to allow the tubing to be more centrally located. Tubing connector 152 can have a depth of at least 0.05, 0.1, 0.15, or 0.2 and/or less than 0.5, 0.3, 0.25, or 0.2 inch or within a range of any of the foregoing endpoints.

FIG. 12C shows a cross section of brush head 148. Brush head 148 may include a plurality of suction ports, including suction port 158 at an oral end (i.e., distal end) and a second suction hole 160 that passes through sponge 156. The suction holes are in fluid communication with suction tubing attached to connector 152. The fluid channel from holes 160 and 158 can be connected through a lofted or upward angled portion of the channel 162.

Connector is preferably positioned centrally relative head 148 to facilitate placement of the head within the receptacle of the adapter 144. The head 148 has a midpoint 164 and the connector 152 has a longitudinal axis 166 that is aligned with midpoint 164. In some embodiments, the longitudinal axis of the tubing connector is off center from the midpoint of the brush head by less than 30%, 20%, 10%, or 5% in width and/or height (where the height is the dimension shown in FIG. 12C and the width is normal to the cross section shown).

Covered Yankauer

Some embodiments of the invention also relate to a covered suction module (e.g., Yankauer) that has an adapter configured to connect with an access port of a positive pressure ventilation mask. Suction module 172 includes a suction appliance 174 slidably connected to a suction appliance adapter 180. Suction appliance 174 includes a tube 176 with a plurality of bends 178a-b. Tube 176 is connected at a proximal end to suction connector 184 for connecting the suction device to suction handle or other source of suction. A sheath 182 (also referred to herein as a cover) is connected to adapter 180 and connector 184. Sheath 182 is bunched due to the adapter 180 being pulled back to expose the working head (suction tip 188). Sheath 182 is welded to connector 184, but can also be connected by other means such as tape or a physical connection such as a snap connect that pinches the sheath.

Figure 13A:
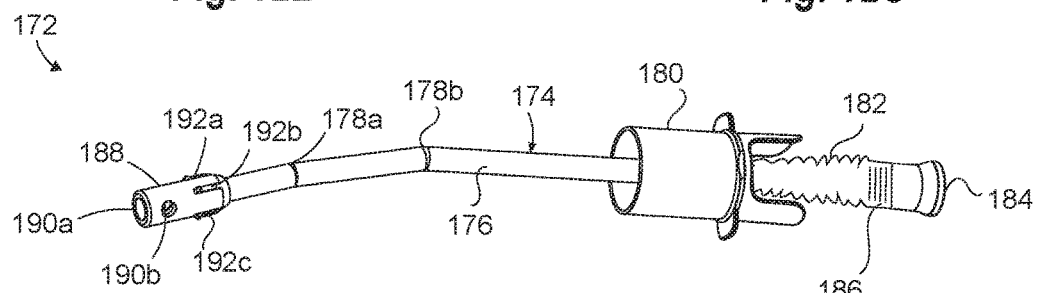
FIG. 13A illustrates a covered yankauer module.
Figure 13B:
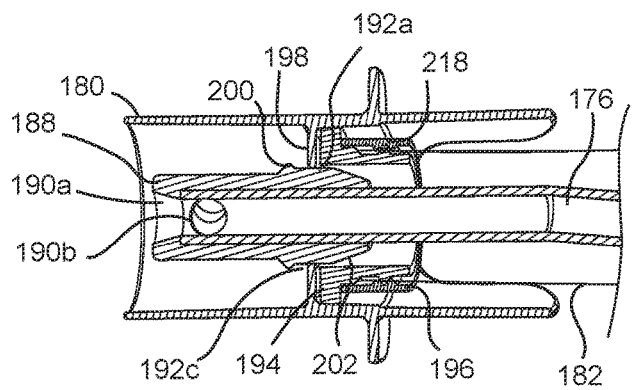
FIG. 13B is a cross section of the adapter and working head of the module of FIG. 13A.
Figure 13C:
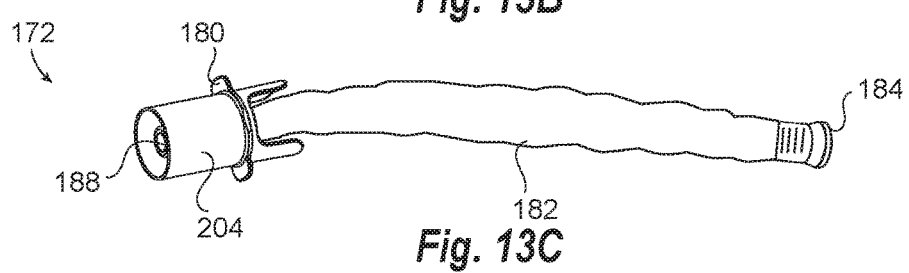
FIG. 13C illustrates the module of FIG. 13A in the covered position.

Suction tip 188 includes a plurality of suction holes 190*a*, 190*b*, and 190*c* (190*c* not shown). Suction head also includes retention features (ribs 192*a-c*) that retain tip 188 in receptacle 204 of adapter 180 when placed in the retracted position as shown in FIGS. 13B and 13C. FIG. 13B is a cross section showing tip 188 in greater detail. Ribs 192*a* and 192*c* are shown with an interference fit to housing member 198, which forms a ring around tip 188 and engages the ribs 192 to provide a desired level of retention. In some embodiments, the tip 188 includes a plurality of ribs. Additional ribs may be used to provide greater stability in the aperture of housing member 198 or to increase the resistance to unwanted pull out. Ribs 192 may have a sloped surface 202 that smooths out the transition of the ribs to the housing member 198, which creates the interference to resist pull out. A stop feature 200 can also be placed on tip 188 to avoid tip 188 from being pulled completely through the aperture of housing member 198.

Sheath 182 provides a cover for tubing 176 when the sheath is in the retracted position. Sheath 182 may be connected to the adapter 180 using an insert 194 and clamp ring 196. Insert 194 is configured to connect with the wall of the adapter. Sheath 182 is positioned over a portion of insert 194 and clamp ring 196 is applied to clamp sheath 182 to insert 194. Bumps 218 on clamp ring 196 engage a bump on insert 194 to provide a friction fit or a "snap on" feature that clamps an end of sheath 182 onto insert 194 and retains the sheath on adapter 180.

FIG. 13C shows suction module 172 in a covered position. In the covered position, tip 188 is housed within receptacle 204 and sheath 182 is extended. In the covered position module 172 can be placed on a surface and tip 188 is protected from contacting the surface and being contaminated or contaminating the surface. Module 172 can be stored by the bedside of the patient and when needed tip 188 can be ejected from receptacle 204 by advancing connector 184 toward adapter 180 to release the tip 188 from housing member 198 and compressing sheath 182.

Figure 14:
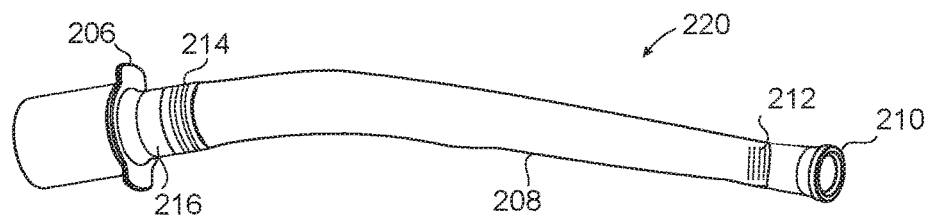
FIG. 14 illustrates an alternative embodiment of a covered yankauer module.

FIG. 14 illustrates an alternative embodiment of the sheath and adapter of a suction device. Suction module 220 includes an adapter 206 configured to form a seal with an access port of mask 10. Adapter 206 includes a tubular grip 216 on an outside portion thereof. An end portion 214 of sheath 208 is attached on the outside surface of tubular grip 216. The attachment may be a heat weld, tape, or any other suitable connection. End 212 is adhered to suction handle connector 210. The connection may be a heat weld, tape, or any other suitable connection (e.g., pinch fit like insert 194 and ring 196 of module 172).

The foregoing suction devices may have adapters with any of the features described herein and may be used on access ports that have a valve or do not have a valve.

Capnometry

Some embodiments of the invention relate to capnometry systems that include a capnometry module having an adapter that connects to an access port of a PPV mask (e.g., mask 10) and allows a capnometry sampling line to be introduced into the mask and/or oral cavity of a patient wearing the mask.

The capnometry module can be used to accurately sample end title $CO_2$ while maintaining ventilator pressure and deliver the $CO_2$ sample to a capnometer for measuring end title $CO_2$ concentration.

Figure 15A:
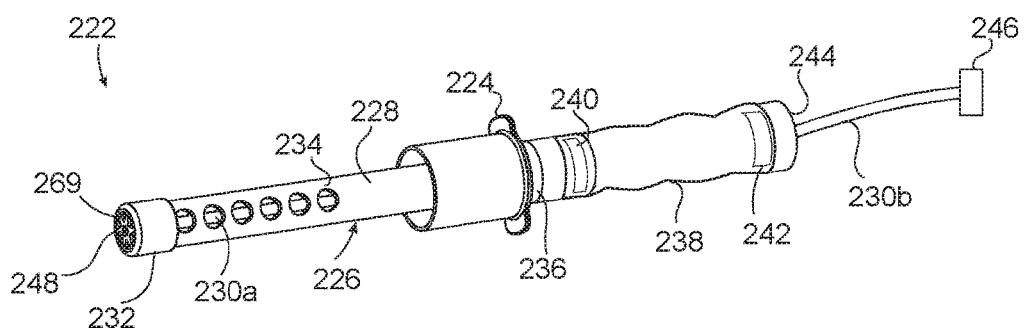
FIG. 15A illustrates a slidable capnometry module in an uncovered position.

FIG. 15A illustrates a capnometry module 222 including an adapter 224 that is configured to attach to an access port of a PPV mask. The adapter can have any of the features of appliance adapters described above and can be used with any access port as described above (e.g., with or without a valve). Module 222 includes a capnometry appliance 226. Capnometry appliance 226 has a support housing 228 that supports and houses an inside sampling line 230*a* that is contiguous with an outside sampling line 230*b* (referred to collectively as sampling line 230). A casing 232 is positioned at an oral end of housing 228. Casing 232 defines an inlet that forms the most distal portion of sampling line 230.

Casing 232 also includes openings at the oral end that are in fluid communication with an interior of support housing 228. Housing 228 includes a series of holes (e.g., the series of six holes ending with hole 234) that allow air to enter and exit housing 228 and serve as a by-pass for air.

The porosity provided by holes 234 and 269 allow a patient to breath while pursing their lips around housing 228 during use. Holes 234 are configured to have at least one hole positioned outside the mouth of the patient and within the mask when attached thereto and in use, such that a patient can breathe through support housing 228 with their mouth closed around housing 228. Air traveling in holes 269 or a portion of holes 234 positioned within the mouth deliver air through housing 228 and into the mask through the portion of holes 234 outside the mouth but inside the mask. Testing has shown that the best $CO_2$ sampling occurs from sampling with the lips closed around the outer tubing and exhaling through the by-pass holes while maintaining pressure in positive pressure mask.

Adapter 224 includes a tubing portion 236 on an outside portion thereof that is used to connect a distal end 240 of a sheath 238. Sheath 238 can be heat welded, taped, or otherwise connected to tubing portion 236. A proximal end 242 of sheath 238 is attached to proximal connector 244 using any suitable connection such as heat welding or tape. Connector 244 forms a seal with outside sampling line 230*b*. Outside sampling line 230*b* includes a sampling line connector 246 that connects to a capnometry system suitable for measuring end title $CO_2$ (not shown). Connector 246 can be a press fit, luer lock, proprietary connector, or any suitable connector for attaching a capnometry sampling line to a capnometry system that can accurately measure $CO_2$. An example of a suitable capnometry system that can be used with the module 222 of the present invention is illustrated in U.S. Pat. No. 5,957,127, which is hereby incorporated herein by reference in its entirety. Another example of a capnometry device that can be attached to the capnometry appliance module 222 is Capnostream™ 35 Portable Respiratory Monitor, by Medtronic™ (Minneapolis, Minn.).

In an alternative embodiment, the capnometry system can be incorporated into the support housing 228 on a proximal end thereof or an outside portion. An example of a capnometry system incorporated into the housing is illustrated in US Patent No. 2005/0245836, which is hereby incorporated herein by reference in its entirety. An additional example of a capnometry device that can incorporated into the support housing 228 of the capnometry appliance module 222 is the EMMA Mainstream Capnometer, by Masimo, Inc. (Irvine Calif.).

Figure 15B:
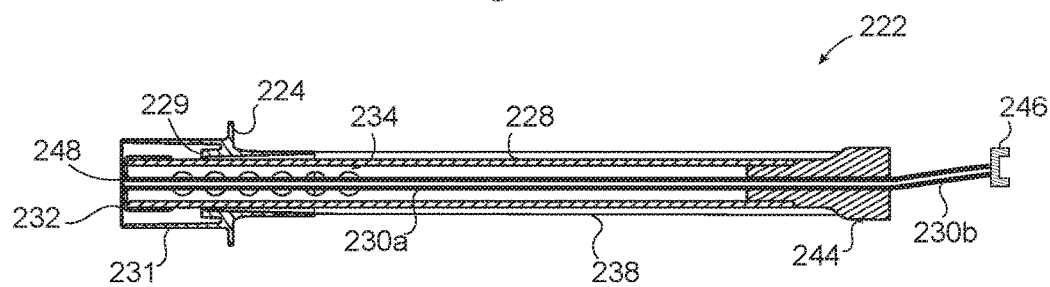
FIG. 15B is a cross section of the module of FIG. 15A in a covered position.

FIG. 15B is a cross section of the capnometry module of FIG. 15A showing the connection between adapter 224 and support housing 228. Adapter 224 includes an aperture 229 that slidably seals against support housing 228. Support housing 228 can have a relatively constant diameter to allow the housing 228 to slide along aperture 229 and maintain a seal. Preferably the gap is in a range as described above with reference to other appliances of the present invention. FIG. 15B shows working head (casing 232 with inlet 248) in a retracted or covered position (i.e., withdrawn into receptacle 231 of adapter 224. With inlet 248 in the covered position, sheath 238 is extended (i.e., no longer bunched or less bunched). In the covered position, a portion of holes 234 are proximal to the aperture 229, which forms the seal with housing 228. However, sheath 238 can be sealed such that pressure in the mask is maintained by aperture 224.

As shown in FIG. 15B, casing 232 supports line 230 in a central position within housing 228. This position is beneficial to avoid saliva from being sucked into inlet 248. Other configurations of inlet 248 can be used where the inlet is internal to the support housing. The inlet to the sampling line may be positioned near the oral end of the housing by less than 50, 25, 10, or 5 mm or greater than or equal to 0, 5, 10, 15 mm and/or within a range of the foregoing.

Figure 16A:
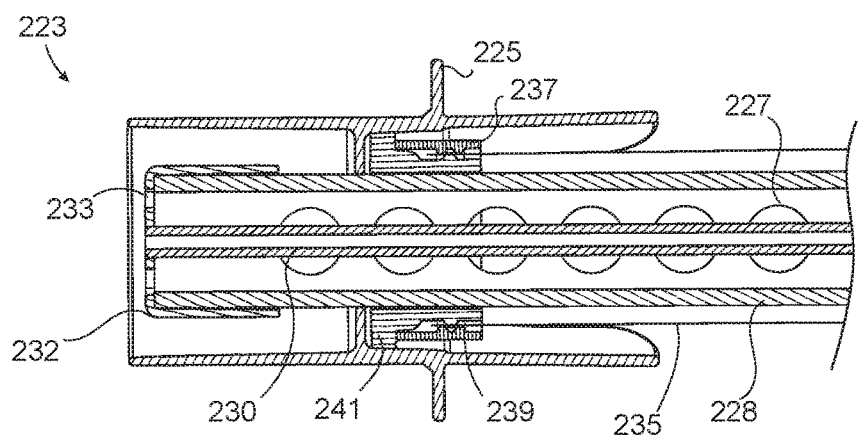
FIG. 16A illustrates a cross-sectional partial view of an alternative embodiment of a capnometry adapter and sampling line.

FIG. 16A is a cross section of a capnometry module 223 according to an alternative embodiment of the invention. Captnometry module 223 includes a support housing 228 with a sampling line 230. Casing 232 shows holes 233 for allowing gas to flow into housing 228. Capnometry module 223 is shown in the retracted or covered position. module 223 includes an insert 241 and clamp ring 237 that attaches sheath 235 in a similar fashion as described above with regard to the yankauer insert.

Figure 16B:
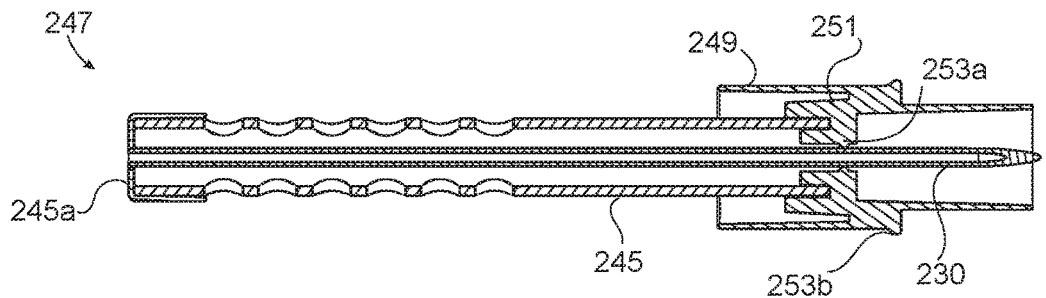
FIG. 16B illustrates a cross-sectional partial view of yet another alternative embodiment of a capnometry module having a fixed support housing.

FIG. 16B describe a capnometry module 247 with a fixed housing 245 relative to adapter 249. Fixed housing 245 is coupled to a housing connector 251 of adapter 249. Connector 251 also includes an aperture 253a through which sampling line 230 passes. Sampling line and aperture 253a form a PPV seal. Adapter 249 also has a seal structure 253b that forms a seal with access port 23 of mask 10. The length of housing 245 is configured to place the oral end 245a within the mouth of a patient when attached to access port 23 of mask 10. Housing 245 is configured to be inserted through a self-sealing and/or self-reverting valve (e.g., valve 42) or may be introduced through valve or other port in the mask, such as a port with a removable cap (FIG. 4A or 4B).

In the foregoing embodiments related to support housing, the housing has sufficient rigidity to be inserted into the mouth. In some embodiments, the housing may be sufficiently rigid to serve as a bite block to prevent a patient from biting through the sampling line. The support housing may have a bend to follow the contour of the mouth or place the inlet near the roof of the mouth of the patient. In some embodiments the sampling line may have a fluid filter for blocking water and allowing the flow of gas.

Some embodiments of the capnometry devices of the invention relate to the use of the ventilator display for outputting $CO_2$ measurements using the capnometry modules of the invention. In this embodiment, readings from the capnometry module are received by the ventilator unit 21 and displayed on display 25.

The present invention relates to software systems in capnometers, nebulizers, and/or ventilators. The ventilation systems may capture a series of end tidal $CO_2$ readings over a period of time. The series can include at least 3, 5, 10, or more readings. Periodicity may be greater than 0.25, 0.5, 1.0, or 2.0 hours and/or less than 24, 12, 6, 3, or 1 hour, or within a range of the foregoing. The change in $CO_2$ concentration may be plotted on a screen typically as mmHg or other pressure. The computer-generated plots can include concentration throughout several breaths or may be a graph of end title $CO_2$ and/or may be a graph of end title $CO_2$ measurements taken intermittently. The ventilator or capnometer may include a warning indicator for threshold parameters that are exceeded relative to the capnometry (e.g., rate of $CO_2$ increases or decreasing or passing an absolute threshold).

The capnometry sampling line adapter can be used with positive pressure ventilation at pressures greater than 4 cm $H_2O$ and bi-level ventilation. U.S. Pat. Nos. 8,146,591, 5,957,127, and US application publication 2012/0272962 describe capnometry systems that can be modified according to the present invention to provide $CO_2$ measurements of a patient on positive pressure ventilation mask. Ventilator system 24 may include an electrical cord that extends the length of ventilation circuit 11 from ventilator unit 21 to mask 10 for use in receiving capnometry readings. The electrical cord may also be used for receiving speech readings from a microphone and/or for performing nebulization.

Endoscope module: The appliance adapter may be an endoscope adapter that includes a sealing structure (e.g., gasket, membrane, or appropriately sized aperture) configured to form a seal with an endoscope. The endoscope may be used to perform an esophagogastroduodenoscopy (EGD) procedure while maintaining pressure in a mask. The opening in the appliance adapter for accommodating the endoscope may be at least 8, 10, or 12 mm and/or less than 15, 13, or 11 mm and/or within a range of any of the foregoing maximum and minimum dimensions.

The foregoing masks, valves, modules, and/or appliances can be used to provide an oral or nasal care system for cleaning the oral or nasal passageways of a patient on a positive air pressure ventilation mask.

While the appliance adapters of the present invention have been illustrated with a self-sealing, self-reverting valve, unless otherwise stated, embodiments of the invention also include performing oral access procedures under pressure with appliances and appliance adapters that are configured to attach to a port with a mere aperture and a removable cap or the like. (see e.g., aperture 22 of US Patent application publication 2010/0116276 to Bayasi).

The appliances described herein may be packaged with the appliance adapter and/or be assembled and/or packaged together. In the case where the seal between the appliance adapter and the appliance is specific to the appliance, the appliance adapters typically needs to be preassembled with the appliance. For example, a suction brush may have a handle on one end and a sponge brush on the other end of a tube and the seal needs to engage the tube. In some cases, pre-assembly of the appliance adapter and corresponding appliance is necessary to avoid the need to find the correct adapter when performing a particular procedure. For instance, when performing an endoscopic procedure an appliance used to introduce anesthetic is best assembled with the adapter to avoid the situation where a practitioner needs to use the appliance to introduce anesthetic and does not have an appliance adapter readily available. Nevertheless, when the appliance is expensive and non-disposable (e.g., an endoscope), the integration of the appliance adapter may not be practical, despite the advantage of doing so.

Intubation Adapter

Figure 17A:
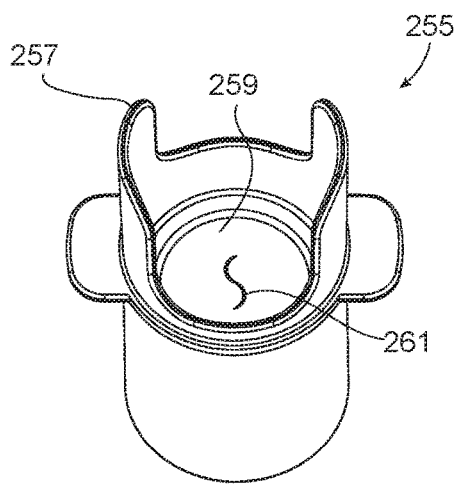
FIG. 17A illustrates a perspective view of an endoscopy adapter.
Figure 17B:
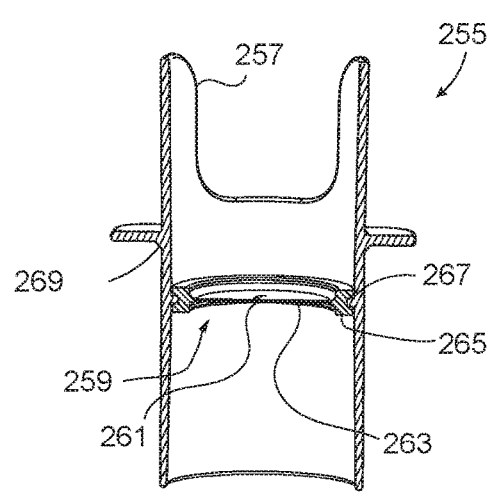
FIG. 17B is a cross section of the endoscopy adapter of FIG. 17A.

Another embodiment of the invention relates to adapters and modules for performing camera-based procedures through a mask. Examples include bronchoscopy, esophagogastroduodenoscopy (EGD) procedure, and intubation. The adapter includes a seal structure for sealing with access port 23 of mask 10. FIGS. 17A and 17B illustrate an example adapter 255 with an adapter body 257 and a membrane 259 that has a slit valve 261. Slit valve 261 is configured to receive an endoscopy device and seal around its perimeter as it is inserted and retrieved from the body of the patient.

Membrane 259 may be a flexible or elastic material. Membrane 259 may be sufficiently elastomeric (e.g., a polyurethane) to allow stretching to place different sized endoscopes while still forming a seal. The membrane may have a hole size that accommodates or stretches to a particular diameter camera (e.g., 5, 6, 8, 10, or 12 mm camera) (or within 1, 2, 3 mm of a traditional camera size). The membrane may also have cross slits to allow a device to be pulled through with more ease.

Membrane 259 may be attached to a bump or annular ridge 267 of adapter body 257. A rim 265 of membrane 259 can be adhered (e.g., solvent bonded) to the adapter wall. membrane 259 has a thin region 263 that facilitates flexibility when an instrument is inserted into slit valve 261. Those skilled in the art will appreciate that there are other types of valve that can be configured within adapter body 257 to form a seal around an endoscopic device.

The endoscopic modules of the invention can have adapters with any of the features of adapters as described herein and can be used with any access ports and masks as described herein.

Figure 18:
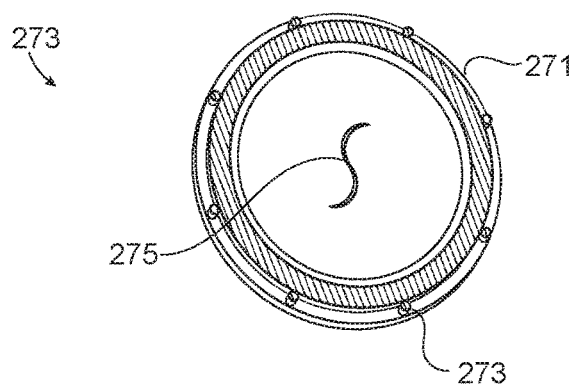
FIG. 18 illustrates a sectional view of an alternative slit valve.

FIG. 18 shows an alternative embodiment of a membrane 273 that is formed from over-molding the membrane with an adapter having holes where the valve material can flow through. Over molded membrane 273 includes a plurality of connecting members 273 that attach rim 271 above and below a protrusion.

Nebulizer

The present invention also relates to adapters, appliance modules and methods for nebulizing a patient on non-invasive positive pressure ventilation (PPV). The nebulizer adapters and nebulizer appliance modules of the present invention can deliver aerosols to the oral cavity of an PPV patient while maintaining pressure and without disconnecting the ventilator circuit to attach the nebulizer.

In a first embodiment, the nebulizer adapter may be an elbow connector that seals with an access port 23 of a mask 10 and connects to a traditional nebulizer. The nebulizer adapter can have any of the features of appliance adapters described above and can be used with any access port as described above (e.g., with or without a valve).

Figure 19A:
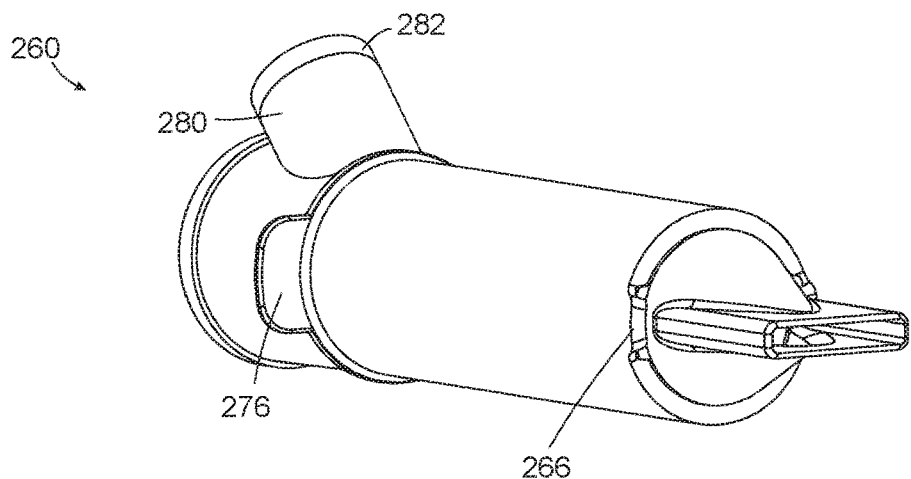
FIG. 19A is a perspective view of a nebulizer module with an adapter configured to form a seal with the mask of FIG. 1.
Figure 19B:
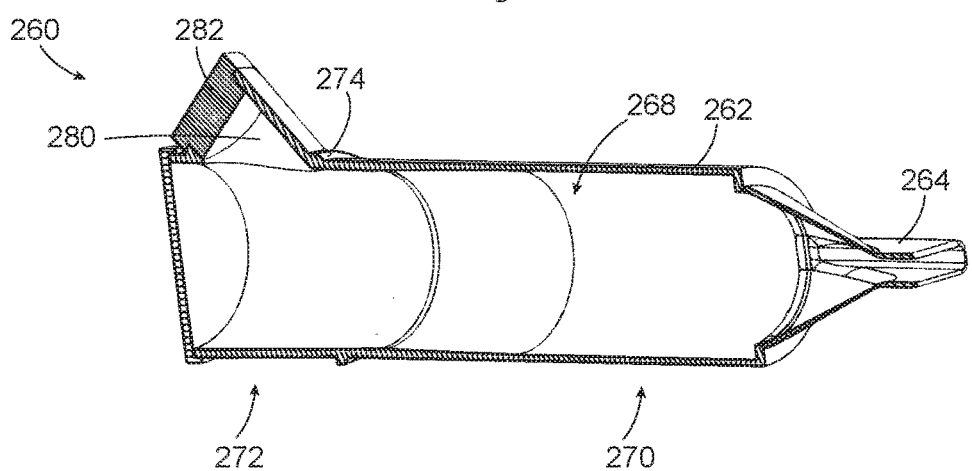
FIG. 19B is a cross section of the nebulizer of FIG. 19A.

The first nebulizer embodiment is illustrated, for example, in FIGS. 19A-19B. Nebulizer adapter 260 connects to an access port 23 of a mask 10 and connects to a traditional nebulizer. An example of a traditional nebulizer that can be connected to the nebulizer adapter 260 is illustrated in U.S. Pat. No. 10/833,932, and is incorporated herein by reference in its entirety. The traditional nebulizer that connects to the nebulizer adapter 260 can include a micro vibrating element portable nebulizer, an ultrasonic nebulizer or a piston pump jet nebulizer. The nebulizer adapter 260 is configured with an inside portion 270 that can be placed through an access port 23 of a PPV mask 10 or an access valve 42 in a port of a PPV mask. The inside portion can be made of a tubular body 262 that defines a tubular chamber 268 that is in fluid connection with a mouthpiece 264. The mouth piece 264 extends from the tubular body 262 and it can be connected by a lock ring 266 or other suitable locking mechanism. The mouthpiece 264 can be removed and exchanged prior to use to allow patients to fit a correct size mouthpiece onto the nebulizer adapter 260. In other embodiments, the mouth piece 264 can be integrated and connect to the tubular body 262 with a pressure fit mechanism or snap fit connections. The tubular body 262, is placed within the mask or into the mouth of the patient. The patient places their lips onto the surface of the mouth piece 264 and can receive treatment from the nebulizer while maintaining ventilation pressure within the mask. Nebulizer adapter 260 can also include an outside portion 272 that is separated by rim 274. Rim 274 can seal with a port 23 having a valve 42, as described above in other appliance modules and adapters. Tabs 276 can be positioned near rim 274. to configure the nebulizer adapter to seal with the valve or port, as described above in other appliance modules.

The outside portion 272 continues the tubular chamber 268. The outside portion 272 is configured with an inlet port 280 (and cap 282) for receiving a traditional nebulizer and is in fluid communication with the chamber 268. A liquid medicament passes through the traditional nebulizer and generates an aerosolized medicament that passes through the inlet port 280 and through tubular chamber 268, and mouthpiece 264. Mouthpiece 264 may be sealed with the users lips and the user breathes in and out slowly. Breathing is continued until the aerosol formation has stopped and the medicament in the traditional nebulizer has been delivered into the patient's respiratory system. The traditional nebulizer is then removed from the inlet port 280 and the nebulizer adapter 260 is removed from the access port 23 and/or valve 42.

In a second embodiment, a nebulizer appliance module 340 includes a nebulizer. The nebulizer appliance module 340 is configured to be inserted into an access port 23 and/or a valve 42 of a PPV mask 10. When the nebulizer appliance module is inserted into the mask 10 aerosol medicaments can be received directly into the mask and/or mouth of the user while receiving ventilated air in the mask. This embodiment, as described in other appliance modules above, will maintain ventilation pressure in the mask while the appliance module is in use. When delivered into the mouth, less medicament will collect on the surfaces of the mask and instead a high percentage of medicament is delivered to the user.

Figure 20A:
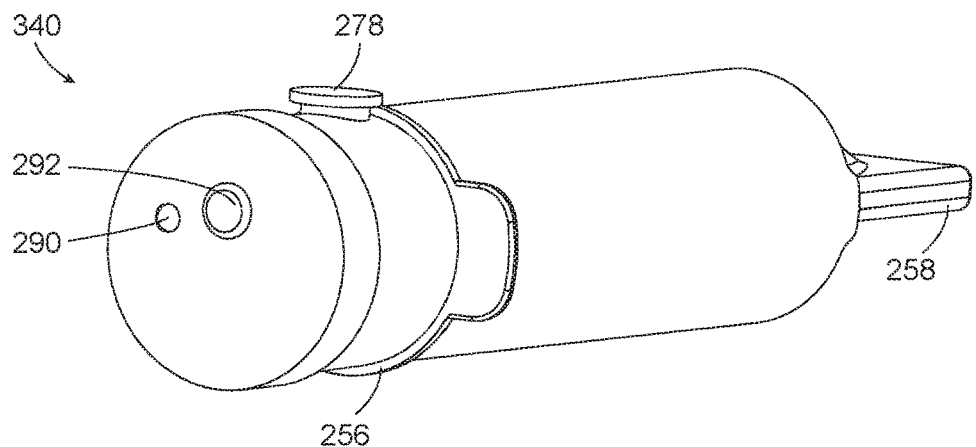
FIG. 20A is a perspective view of a nebulizer module according to an alternative embodiment of the invention.
Figure 20B:
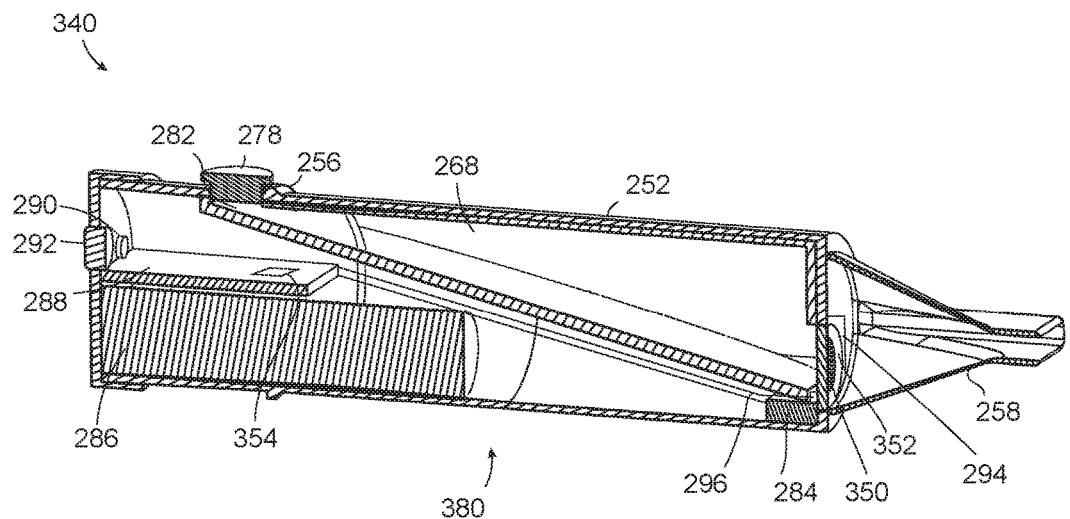
FIG. 20B is a cross section of the nebulizer module of FIG. 20A.

FIGS. 20A and 20B illustrate an embodiment of a nebulizer appliance module 340. The nebulizer appliance module includes an adapter body 252 that defines an inner fluid reservoir 254, a module chamber 380, a sealing rim 256, and a mouthpiece 258. In an alternative embodiment, the mouthpiece 258 can be removable and exchangeable. The mouthpiece 258 is configured to connect to the tubular chamber 268, as described in the nebulizer adapter 260 above. The inner fluid reservoir extends from the inner portion and the outer portion of the adapter body 252. The fluid reservoir has an opening or inlet port 282 configured to receive liquid medicament and has a reservoir cap 278 configured to seal the inlet port 282 of reservoir 254. Reservoir 254 can hold a liquid volume of at least 2 ml, 4 ml, 6 ml, 8 ml, or 12 ml and/or less than 50 ml, 30 ml, 25 ml, or 20 ml, and/or within a range of the forgoing endpoints. A module chamber 280 houses a battery 286, circuit board 288, controller leads 296, and a fluid sensor 284. The fluid sensor is in fluid communication with the reservoir 254 and is configured to turn off the power to the aerosol generator 294. The aerosol generator is at or near to the distal end of the adapter body 252 and is in fluid communication with the inner fluid reservoir 254. The aerosol generator 294 comprises a vibratable member 300 (such as a micro vibrating element) and a piezoelectric element 302. The vibratable member 300 and piezoelectric element 302 can have a plurality of tapered apertures extending between the upper and lower section of the distal end of the adapter body 252.

FIGS. 20A and 20B illustrate a simplistic view of a nebulizer circuitry, parts, and connections. A Power switch 292 and LED 290 indicator are located on the proximal end of the adapter body 252. See U.S. patent Ser. No. 10/833,932 for a detail description of the circuitry, parts, and connections of a micro aerosol generator system, which is hereby incorporated herein by reference.

The input from the power switch 292 is received by a control unit 304 on the circuit board 288. The circuit board 288 uses the input to turn on and off the aerosol generator. The aerosol generator causes the piezoelectric element 302 to vibrate the vibrating member 300.

This vibration of the vibratable member 300 causes the liquid medicament to pass through the apertures of the vibrating member 300 where the medicament is aerosolized by the ejection of small droplets of medicament. The aerosolized droplets of medicament flows through the mouthpiece 258 and into the oral airway to be received by the respiratory track of the user.

Figure 21:
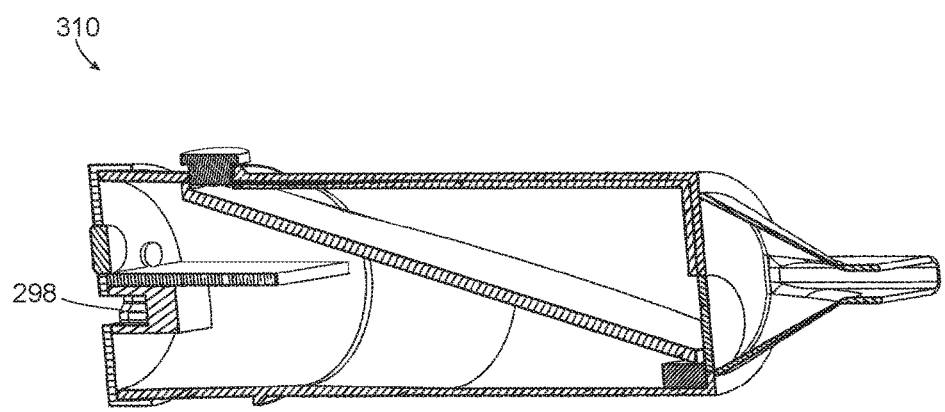
FIG. 21 is cross section of a nebulizer module according to yet another embodiment of the invention.

A nebulizer system can be powered by a battery 286 that is housed in the module chamber 280 or it can be powered by a controller that plugs into a nebulizer system on the proximal end of the adapter body 252. FIG. 21 illustrates a nebulizer appliance module 310 that is configured with a controller connector 298 and is configured to receive a control signal from a controller (not shown).

The nebulizing fluid can be delivered to the patient in coordination with the inhalation of the patient. Delivery of the medicament during inhalation can be controlled by varying the carrier gas. At the time or just before the patient inhales, the carrier gas pressure can be increased to cause an increase in nebulization and then decreased on exhalation. In some embodiments the carrier gas pressure is varied using the pressure variation delivered by a bi-level ventilator. In some embodiments, the timing of the carrier gas delivery can anticipate the time needed to cause nebulization to flow into the mask or oral cavity coordinated with when the next inhalation in expected to happen.

Microphone System

Figure 22:
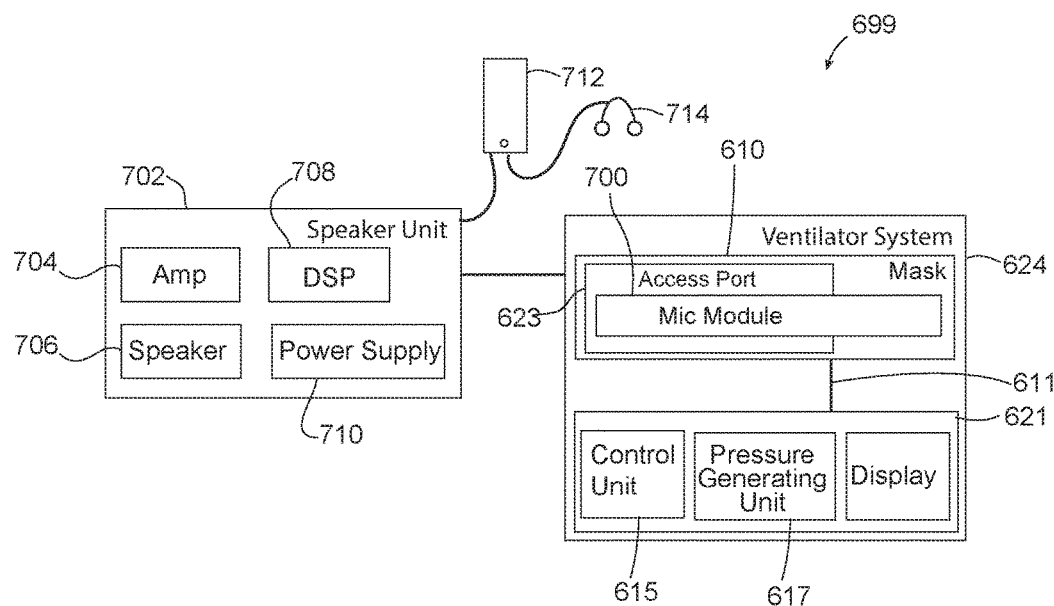
FIG. 22 is a block diagram of a positive pressure ventilator microphone system that includes the mask of FIG. 1A.

FIG. 22 illustrates a microphone system 699 that includes a ventilator system 624 including mask 610, access port 623, and a microphone module 700. Microphone module 700 includes an adapter that connects to the access port 623. Ventilator system 624 also includes a ventilator unit 621 that connects to inlet 630 of the elbow 626 via a flexible hose (not shown) to form a ventilator circuit 611. The ventilator includes a pressure sensor that senses pressure in the system and is used by control unit 615 to control pressure by driving a pressure generating unit 617. Parameters of the ventilator can be displayed on display 617 and input received through a user interface (not shown). Ventilators used with the PPV masks of the invention are preferably bi-level pressure ventilators (or alternatively continuous pressure ventilators). Bi-level ventilation is typically important for critical care patients.

Figure 23:
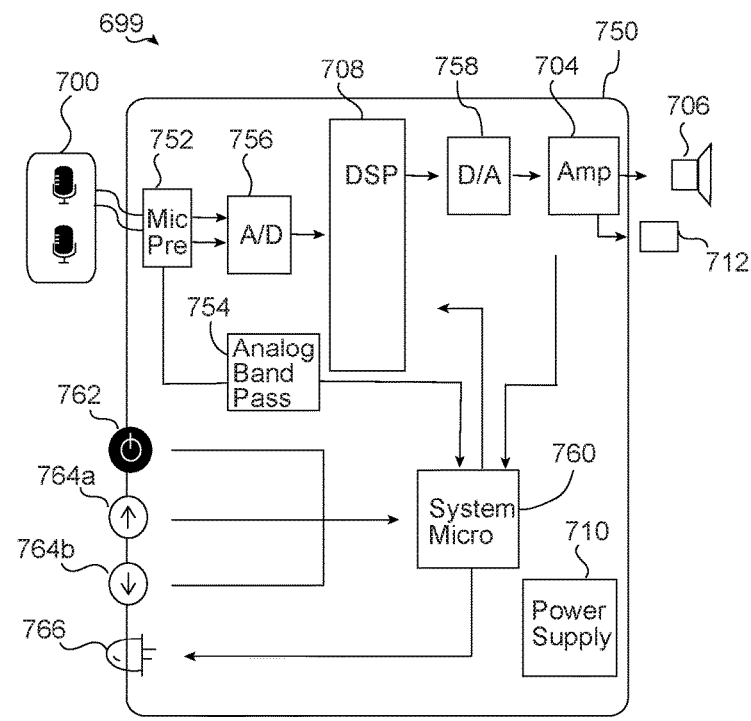
FIG. 23 is a cross section of a microphone module in an elbow connector of FIG. 1A.

FIG. 23 describes a hardware layout for microphone system 699 including a microphone module 700 and a powered audio processing system 750. The audio processing system may output to a loud speaker 706. Loudspeaker 706 may be a bedside. Bedside speaker can be advantageous when placed near the patient because the origination of the sound will be more likely to sound like it is coming from the person in the bed (i.e., more natural). More natural speaking can be important to critically ill patients since they are frequently at end of life and desire to communicate with loved ones for the last time.

Module 700 includes the plurality of microphone elements, preferably at least two microphones. The audio processing system 750 includes a microphone preamplifier 752, analog to digital converter 756, digital signal processor 708, digital to analog converter 758, power amplifier 704, system microprocessor 760, power supply 710, power on/off switch 762, volume up and down buttons 764a and 764b, power indicator LED 766, and a signal output 712.

Figure 24:
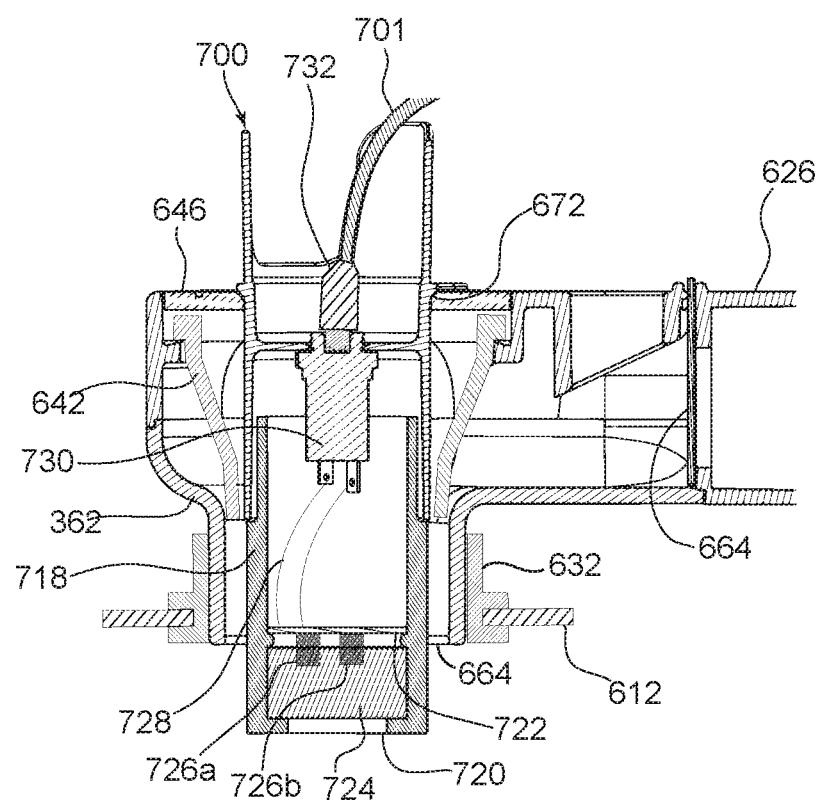
FIG. 24 is a component diagram of a portion of the microphone system of FIG. 22.

FIG. 24 is a cross section of a mask 610 and mic module 700. FIG. 24 shows an adapter 718 that has an extension housing 718 that extends the housing of the adapter in the distal direction (i.e., toward the oral end). At the oral end, the extension housing 718 has an opening 720 that faces the mouth of a person when the adapter is positioned in mask 610.

Adapter 718 and its extension housing 718 can disconnect for placing components of the microphone module into the housing and assembling the housing around the microphone module components (e.g., a press fit or a snap connect. The housing is preferably configured to place the microphone within the cavity of the mask close the patient's mouth, which has been found to be important in some embodiments for obtaining suitable signal to noise ratio for performing accurate digital signal processing.

The length of extension housing 718 is selected to place the opening near the mouth. Preferably less than 3, 2, 1.5, or 1 inch and/or greater than 0.25, 0.5 or 1.0 inch and/or within a range of the foregoing. The length of the adapter and housing as measured from the opening of the access port to the oral end of the microphone module may be greater than 1, 1.5, 2, 2.5, 3 inch and/or less than 6, 5, 4, 3.5, 3, 2.5, or with a range of the foregoing.

Adapter 716 is positioned in the access port which extends from ring 646 and opening 664 of elbow 626. Microphone module 700 extends through opening 664 so as to place the microphone beyond mask body 612 and its adjacent structure, swivel 632. Moving the microphone out of the opening 664 and/or away shell 612 has been found to substantially improve the signal to noise ratio. In one embodiment, the adapter is configured to couple with the access port and place the opening 720 to the microphone at least 0.25, 0.5, 0.8, or 1.2 inch inside the mask from the center point of opening 664 (i.e., the inside opening of the access port). The opening 720 of microphone module is preferably facing a mouth region of the person so as to receive direct sound from speech from the mouth.

A plurality of microphone elements 726a and 726b (collectively 726) are mounted on circuit board 722. Microphone elements 726 can be an electret or a MEMS. Electrets can be preferred for their high sound pressure levels, which has been found to be important in the NIV Mask environment. MEMS can be preferred for minimizing size of the module and availability of bottom firing elements. The microphone element may be an omnidirectional microphone or a directional microphone. Preferred elements have a high dynamic range and/or high sound pressure level. Digital MEMS (a/d converter on mic board) are also suitable, which can be used to reduce electrical noise from hospital equipment placed near the bedside. Digital MEMS may also be useful for having more microphone elements with fewer wires since the signals from different elements can be transmitted on the same wire. In some embodiments the microphone element may be an active mic (power sent to the mic). The microphone element may also have its own pre-amp before the preamp in the audio processing system. A pre-amp on the microphone can reduce clipping of the microphone, which can be a particularly difficult problem with voice amplification on positive pressure masks due to the increase in pressure. Although not preferred, some embodiments can use a single microphone element. Noise cancellation with a single microphone element can require additional computation power. Noise cancellation can be performed using the frequency domain to identify non-speech elements of the signal.

Preferred embodiments of the system use two or more microphone elements. The two or more elements can perform processes where coincident signals are useful, such as in discriminant noise cancellation. Two microphone elements may be mounted on a board and/or within housing. The microphone elements may be differently specified microphone elements or preferably identical specification mic elements. The mic elements may be mounted in the same plane, off plane, and/or at different angles. Same plane microphones may facilitate manufacturing while differently angled microphones may provide better discernment of off-axis signals. Detecting off-axis signals can facilitate detecting turbulent vs coincident sounds.

In a preferred embodiment the microphone has a relatively high max sound pressure level. The closeness of the microphone in the mask and the relatively high pressure in the mask causes surprisingly high sound levels even for patients talking moderately loud or quietly. The microphone module may include a sound attenuating material create an effective sound pressure level that avoids microphone clipping for a person talking at 50, 60, or 70 db. For purpose of this invention, unless otherwise indicated, effective sound pressure level is the sound pressure level of the microphone plus the decibels by which the sound attenuating material attenuates sand. The sound attenuating material may have a thickness and/or a density that prevents clipping of a microphone in the housing when placed in the mask. The sound attenuation of a foam may depend on its density and thickness. The thickness may be An example of a suitable electret may have the following specifications plus or minus 5%, 10%, or 20% for any: −42±3 dB RL=2.2 kΩ Vcc=2.0 v (1 kHz 0 dB=1 v/Pa) Impedance Max. 2.2 kΩ 1 kHz (RL=2.2 kΩ) Frequency 50-12000 Hz Current Consumption Max 0.5 mA Operating Voltage Range 1.0-10 V Max SPL (dB) 120 dB S/N Ration More than 58 dB Sensitivity Reduction 2.0-1.5V Variation less than 3 dB Storage Condition −20~+60° C.; R.H.<45%~75% Operating Condition −10~+45° C.; R.H.<85%.

In a preferred embodiment the microphone element has a diameter less than 0.8, 0.5, 0.3, 0.25, 0.2, 0.15 and/or greater than 0.03, 0.05, 0.1, or 0.15 inch and/or within a range of the foregoing. The microphone elements may be a directional microphone or an omni directional. Microphone elements 726 are selected to have a low self-noise, a high max SPL, and/or a high dynamic range and/or a small size. For purposes of this invention, the SNR is measured with a standard reference pressure of 94 dB SPL (1 Pa) at 1 kHz. In one embodiment, the dynamic range is at least 80 db, 85 db, 90 db, or 95 db, the SNR is at least 60, 65, or 70 db and/or the sound pressure level of the microphone element is at least 80, 85, 90, 95, 100, 105, 110, 115, 120 and/or less than 160, 150, 140, 130 or within a range of any of the foregoing endpoints (at the conditions set forth above for the suitable electret).

Module 700 can include an attenuator 724. Placing the microphone close to the patient's mouth can cause excessive gain or clipping of the microphone. To reduce the power of the vocalization, a sound attenuating material can be placed between the mic elements and the mouth of the patient. The sound attenuating material may be a dense or thick foam. A high dynamic range microphone placed near the mouth and attenuated can produce a signal that is suitable for processing in a digital signal processor. In one embodiment the attenuator may be a foam with a density of at least 2, 2.5, 3, 4, or 5 lb ft$^3$ or less than 10, 8, 7.5, 7, or 6 lb ft$^3$. In a preferred embodiment, attenuator is a biocompatible foam. Traditional foam windscreens typically have a density less than 2 lbs ft$^3$, has been found to not be sufficient to attenuate the power of the voice when using a high dynamic range or high max SPL mic placed near the mouth in a PPV mask. In one embodiment, the attenuator reduces the sound pressure level across the attenuator by at least or less than 3, 5, 10, 12, 15, or 20 db or a range thereof.

Wires 728 connect board 722 with jack 730. Jack 730 is mounted to the body of adapter 716 and is in electrical communication with cable connector 732 and cable 701 is inserted into jack 730 and extends in the proximal direction away from jack 730. Jack 730 may form a PPV seal with adapter to maintain pressure in mask 610. Alternatively cable 701 can be mounted in adapter 716 and electrical coupled to mic elements 726 inside adapter 716. Or as described below, the seal can be between board 722 and extension 718 of adapter 716.

Figure 25A:
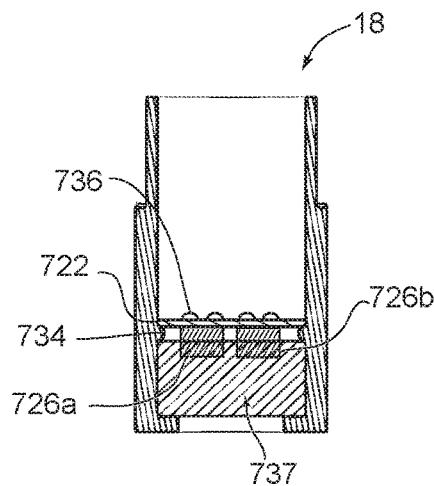
FIG. 25A illustrates a microphone enclosure with microphone elements.

In some embodiments, most or all of the electrical components are isolated from the distal opening of the microphone housing to prevent ventilation gases from reaching the isolated electrical components. FIG. 25A shows an extension housing 718 with a cavity 737 bounded by circuit board 722 and walls of extension 718. Cavity 737 has an opening 720 at the oral end. Microphone elements 726*a* and 726*b* are disposed within cavity 737 as well as an attenuator material. Circuit board 722 can be sealed to annular feature 134 on the wall of extension housing 718. Any technique can be used to form the seal including press fit, heat welding adhesion, snap connects and any other connection suitable for use with connecting a board to a housing. Cavity 737 may be coated with a biocompatible polymer prior to or after mounting microphone elements 726*a* and 726*b*. Microphone elements can be connected with pins that are soldered to form solder bumps 736.

Figure 25B:
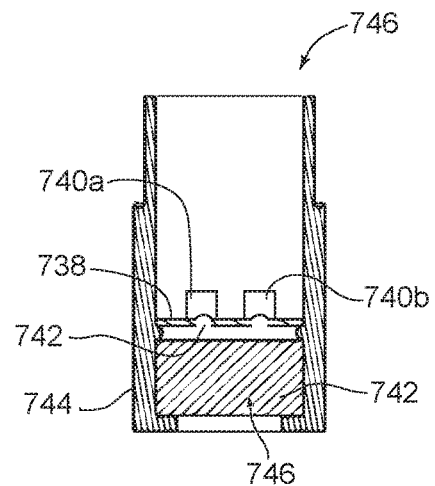
FIG. 25B illustrates an alternative embodiment of a microphone enclosure with microphone elements.

FIG. 25B illustrates an embodiment of a sealed microphone cavity similar to FIG. 25A but with bottom firing microphones. Board 738 is mounted or sealed to housing of extension 748 to form cavity 747. Microphone elements 740*a* and 740*b* are mounted on the proximal side of board 738 opposite cavity 747 and opening 720. Holes (e.g., hole 742) are formed in board 738 to allow sound entering opening 720 to pass through board 738 and into the bottom of elements 740. Microphone elements 740 may be flow soldered to board 738 prior to being secured in extension 746. Cavity 747 may be sealed with a biocompatible coating prior or after mounting bottom mount microphone elements 740*a* and 740*b*.

Figure 26:
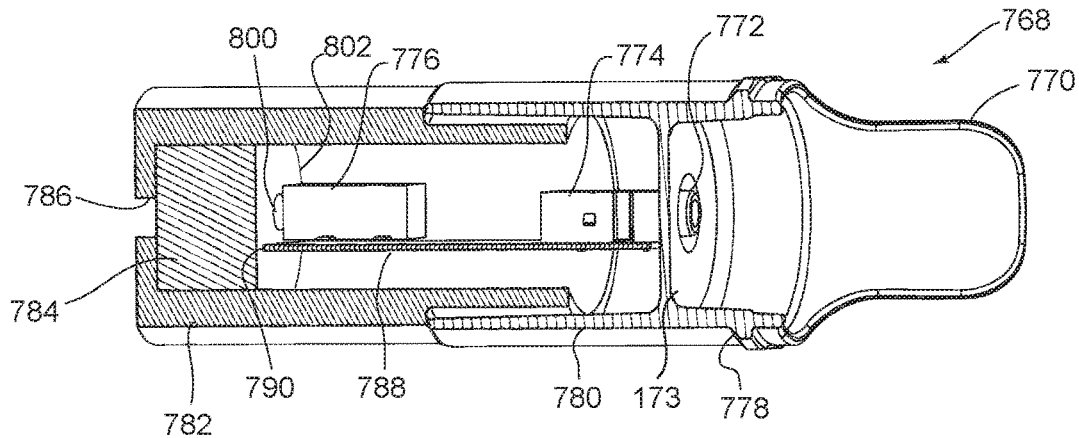
FIG. 26 shows another embodiment of a microphone module.

FIG. 26 illustrates yet another alternative embodiment of a microphone module 768. Module 768 includes an adapter 770 with an extension housing 780 attached thereto. Adapter 770 includes a seal structure 178 configured to connect to and seal with a 623 in mask 610. Module 768 includes an opening 786 at an oral end thereof and an attenuator 784 disposed within housing 782. A microphone element 800 is mounted facing opening 786 using a connector 776. Board 788 extends from a distal end to wall 773 of adapter 770. Board 788 can be used to avoid using wiring between mic elements and the connector 774 in wall 773. Connector 774 can include a jack 772 for attaching a cable. Module 768 can have a wall (not shown) that originates at position 802 and extends transverse and around microphone element 800 to provide an aperture to seal microphone element 800.

Figure 27:
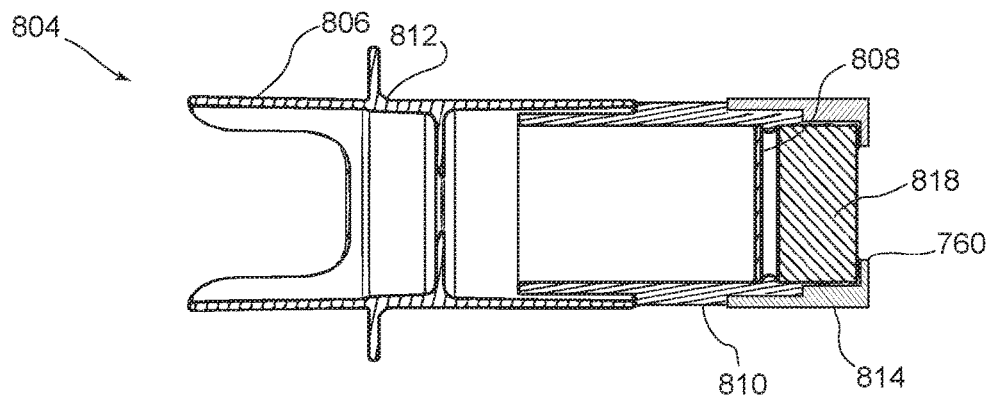
FIG. 27 shows a microphone housing with a removable foam end.

FIG. 27 describes yet another embodiment of a module 804 that includes an adapter 806 with a seal structure 812 and a housing extension 810 and a board 808. A removable cap provides access to attenuator 818 to make it easily replaceable. Replacing attenuator 818 or a foam can be advantageous to avoid harboring bacteria. This can be advantageous in a critical care setting where infections are particularly challenging for patients to recover from. The cap can have a press fit, threads or any other mechanism suitable for connecting the cap to the housing.

In some embodiments, the audio processing system, speaker, and battery power can be built into the housing of the microphone adapter to avoid having cords or other elements attached to the patient. This embodiment is preferred where small speakers and limited power are suitable and where cords are particularly problematic. In other embodiments, the microphone module connects to a speaker housing and/or amplifier housing including the amplification and signal processing components.

Additional details regarding the microphone system can be found in applicant's provisional patent application Ser. No. 62/612,303, filed Dec. 29, 2017, which is hereby incorporated herein by reference.

Ventilator GUI and Computer Implemented Methods for Controlling a Ventilator Circuit During Oral Care and Tracking Oral Care Events The present invention also relates to using ventilator system 24 including ventilator unit 21 and embedded software systems in ventilator unit 21 for providing ePAP and iPAP settings during oral care and/or for monitoring and tracking oral care. For instance, the ventilator unit 21 may have an oral care setting that allows a clinician to select changed ventilator settings or change the way in which the ventilator calculates a setting such as breathing rate or the alarm. For instance, when oral care suctioning is performed the pressure decreases, which can trigger the ventilator to breath sooner. The oral care setting can compensate for this effect by calculating a slower breathing rate while suctioning is being performed. In some embodiments, the ventilator alarm can be set at a higher leak rate to compensate for false alarms caused by suctioning. In some embodiments, the oral care setting may have a time limit. In another embodiment, the ventilator 21 may have a pressure sensor that detects the change in pressure and determines that the change in pressure is a result of suctioning. For example, the pressure sensor data can be analyzed to identify a rate of change and/or a degree of change that is characteristic of suctioning. For example, the rate of change will depend on the characteristics of opening the on/off switch in the suction handle and the amount of change will depend in large part on the diameter of the tubing used for an oral care appliance. The ventilator system can process the pressure sensor data and detect changes that are indicative of leak and compensate for the leak by driving the pressure generating unit and/or prevent an alarm from sounding. The pressure sensor system may take a pressure measurement at least 1, 10, 100, 500 times per second.

The ventilator software may also track oral care activities and/or provide an indicator (e.g., reminder or a warning) for under-performing or over-performing oral care. In some embodiments, the indicator is based on a hospital standard. The ventilator software may record time of day, duration, and/or person that provides oral care for a particular patient. The ventilator may automatically calculate a next time to perform oral care based on when a previous oral care was performed.

Methods for Using an Appliance while Maintaining Positive Pressure

Some embodiments of the invention relate to accessing the oral airway to perform procedures while maintaining positive pressure and performing oral care on a patient while maintaining sufficient pressure to provide clinically relevant breathing assistance and/or to maintain an open airway in the patient.

(i) Oral Care: The present invention also relates to methods for providing oral care through a non-invasive positive pressure ventilation mask. The method includes (i) providing a positive pressure ventilation mask including where the mask includes, a mask body defining a cavity and having a peripheral seal configured to engage a wearer's face, an access valve providing external access to the cavity, and an inlet for receiving pressurized air; (ii) pressurizing the mask to a pressure of at least 200 Pa using a ventilator system (alternatively to a pressure of at least 1, 2, 5, 10, or 15 and/or less than 35, 30, 25, 20, 15 cm $H_2O$, and/or within a range of any of the foregoing pressures); and (iii) introducing an oral appliance into the cavity through the valve and maintaining a pressure of at least 200 Pa (alternatively a pressure of at least 2, 5, 10, or 15 cm $H_2O$ and/or less than 35, 30, or 25 cm $H_2O$) while performing an oral or nasal care procedure.

In a preferred embodiment, a bi-level ventilator is used and the two different pressures of the ventilator are different by at least 2, 4, 6, or 8 cm $H_2O$ and/or less than 20, 15, or 10 cm $H_2O$.

The desired pressure is maintained by providing an appliance with an adapter that couples to the mask and maintains sufficient seal, or by providing a valve in the mask that will seal around the appliance, or both. For example, in some embodiments, the self-sealing and/or self-reverting valves described herein may be used for performing oral care. Alternatively, or in addition, an appliance adapter as described herein may be used with a port with a removable cap (see e.g., US Patent application publication 2010/0116276 to Bayasi). In either case, the valve opening or port is preferably positioned over the oral cavity and/or has a relatively wide opening (e.g., the dimensions described above) to facilitating oral cleaning, which requires a large degree of manipulation to be performed properly.

In some embodiments, the oral care procedure includes applying a cleaning fluid to a least a portion of the oral cavity and suctioning excess cleaning fluid. The cleaning fluid may be water, mouth wash, or toothpaste. The cleaning fluid may include a cleaning agent such as a debriding agent or an anti-microbial agent. For example, the cleaning fluid may include a solution having an anti-microbial (e.g., cetylpyridinium chloride) in sufficient concentration to clean the oral cavity. For example, an antimicrobial may be added in a concentration of at least 0.01, 0.05, or 0.1, or 0.5% and/or less than 1.0, 0.5, or 0.1% or within a range of the foregoing. For purposes of this invention, anesthetics suitable for numbing the throat (e.g., for performing intubation) are not a suitable "cleaning fluid" for performing the oral care described herein.

When cleaning the oral cavity, the cleaning fluid is typically applied to a majority of the surface of the mouth. In one embodiment, the cleaning fluid is applied to a least a portion of the gums and/or teeth.

The cleaning fluid may be provided in a container and a sponge on a stick may be dipped into the container to absorb an amount of solution. The sponge and fluid is then inserted into the oral cavity through a valve in the mask and the sponge is used to scrub surfaces of the mouth of the patient, include the teeth, gums, tongue, and/or cheeks of a patient.

In some embodiments, the fluid may be delivered using an appliance that also includes suction. The surface can be scrubbed using the sponge and fluid and fluid that is squeezed onto the surface can be suctioned through a shaft of the appliance. In one embodiment, the appliance can include a selectable suction controller such that the user performing the cleaning can select when to apply suction as the appliance is being used. For example, the appliance can have an access port to the suction channel and the port can be opened and close by the user covering it with his or her finger. In some embodiments, the appliance may include bristles for more rigorous cleaning of surfaces (e.g., teeth).

The appliance inserted through the valve may have a shaft that is rigid and straight, which allows it to be moved in an appliance adapter while maintaining a seal. However, in some embodiments, the shaft may have a bend to allow easier access to the inside surface of the teeth.

The cleaning agent may be water or a mouth wash. A paste or other carrier can also be used. However, where a sponge appliance is desired, the cleaning agent is preferably a fluid.

Alternatively, or additionally, the method may include applying a wetting agent to the oral or nasal cavity. In some embodiments, the wetting agent may include a moisturizer (e.g., methylcellulose). In some embodiments, the wetting agent includes ice or ice water.

The method can include applying any anti-microbial or moisturizer known to be suitable for application to the mouth or nose for purposes of cleaning or wetting. Where a fluid is applied, the appliance used to deliver the fluid preferably includes suction. The use of an appliance to suction is important since the positive pressure is maintained during the treatment and it is important to avoid aspiration of excess fluids.

In some embodiments, the method is a treatment of the nose, including treating epistaxis, lubricating the nasal cavity, and/or treating rhinorrhea. The appliance may also be used to treat itching or other irritations or discomforts. For example, a sponge on a stick can be used for mild scratching of the skin.

The ventilation system used to provide positive air pressure can be any known in the art, including volume ventilators, pressure controlled ventilators, bi-level positive airway pressure devices, continuous positive airway pressure devices, fixed pressure device, automatic positive airway pressure device, and expiratory positive airway pressure device.

The pressure during the oral or nasal care procedure is maintained at acceptable pressures for the patient such as a pressure of at least 300 Pa, 400 Pa, 500 Pa, or 600 Pa and/or less than 5000, 4000, 3000 Pa and/or within a range of the foregoing during use of an appliance in the valve.

To perform proper oral care, the valve has an opening of a suitable diameter. In one embodiment, the valve has an opening with a diameter of at least 5, 10, 15, 20, or 25 mm and/or less than 60, 50, 40, 30, or 20, and/or within a range of the foregoing sizes. During use of the appliance in the mask the valve may be opened to a width within the foregoing ranges.

The method may be performed with a valve incorporated into the body of a mask. Alternatively, the valve may be incorporated into a conduit where the pressurized air flows into the inlet of the mask and the valve is configured to provide access to the cavity through the pressurized air inlet.

Unlike cleaning or wetting methods described in the prior art, the methods of the present invention can be carried out without removing the mask and without exceeding the maximum leak rate for the ventilator. This approach provides substantial benefits identified and recognized by the inventors. For example, by maintaining a suitable seal during use, the oral care adapter can be used on patients who are too ill to have the mask removed for oral care. In addition, oral care may be performed by the patient themselves or a nurse, rather than a respiratory therapist (Although the RT or doctor can also perform the oral care). By facilitating a system that can be used by patients and nurses, the care providers can have sufficient resources to perform oral care on a regular basis, without substantially increasing the cost of care.

Another embodiment of the invention relates to performing an esophagogastroduodenoscopy (EGD) procedure under pressure. The method The method includes (i) providing a positive pressure ventilation mask including where the mask includes, a mask body defining a cavity and having a peripheral seal configured to engage a wearer's face, an access valve providing external access to the cavity, and an inlet for receiving pressurized air; (ii) pressurizing the mask to a pressure of at least 200 Pa using a ventilator system (alternatively to a pressure of at least 1, 2, 5, 10, or 15 and/or less than 35, 30, 25, 20, 15 cm $H_2O$, and/or within a range of any of the foregoing pressures); and (iii) introducing an endoscope into the cavity through the valve and maintaining a pressure of at least 200 Pa (alternatively a pressure of at least 2, 5, 10, or 15 cm $H_2O$ and/or less than 35, 30, or 25 cm $H_2O$) while performing an EGD procedure. The endoscope may have suction and a working channel and/or a plurality of working channels and a diameter of at least 8 mm. The endoscope may include an appliance adapter configured to engage a port of the mask and seal the endoscope while allowing the endoscope to be advanced and/or manipulated in the patient's airway through the appliance adapter and the mask while maintaining the desire pressure.

The present invention also relates to methods performed using a bite block adapter. The method includes (i) providing a positive pressure ventilation mask including where the mask includes, a mask body defining a cavity and having a peripheral seal configured to engage a wearer's face, an access valve providing external access to the cavity, and an inlet for receiving pressurized air; (ii) pressurizing the mask to a pressure of at least 200 Pa using a ventilator system (alternatively to a pressure of at least 1, 2, 5, 10, or 15 and/or less than 35, 30, 25, 20, 15 cm $H_2O$, and/or within a range of any of the foregoing pressures); and (iii) introducing an endoscope into the cavity through the valve and maintaining a pressure of at least 200 Pa (alternatively a pressure of at least 2, 5, 10, or 15 cm $H_2O$ and/or less than 35, 30, or 25 cm $H_2O$) while performing an EGD procedure. The endoscope may have suction and a working channel and/or a plurality of working channels and a diameter of at least 8 mm. The endoscope may include an appliance adapter configured to engage a port of the mask and seal the endoscope while allowing the endoscope to be advanced and/or manipulated in the patient's airway through the appliance adapter and the mask while maintaining the desire pressure.

The present invention also includes methods for using any of the other appliance modules or adapters as described herein. Applicant's co-pending PCT Application No. PCT/

US2016/039117 is hereby incorporated herein by reference in its entirety. Any of the forgoing methods may be carried out using an appliance adapter to deliver an appliance through the valve.

EXAMPLES

The following examples provide specific configurations of systems, modules, and methods that can be carried out according to embodiments of the inventions described herein.

Example 1 (Appliance Module): A positive pressure ventilation (PPV) appliance module, comprising: a PPV appliance adapter having a first seal surface and a second seal surface, the first seal surface configured to form a first PPV seal with an access port of a PPV mask when attached thereto, the second seal surface defining an appliance aperture that forms a second PPV seal with an appliance, the appliance adapter having an inside portion on a first side of the first and second seals and an outside portion on a second side opposite the first side, wherein the inside portion is exposed to the pressure of the ventilator and the outside portion is exposed to a pressure external to the PPV mask when the adapter is attached thereto; the appliance including an elongate member having a distal end and a proximal end, wherein the distal end includes a working head, the working head having a larger diameter than the appliance aperture, which prevents the working head from being passed through the appliance aperture, wherein the working head is positioned on the first side of the adapter and the proximal end is positioned on the second side of the adapter.

Example 2: The module of any of the foregoing examples, wherein (i) the appliance includes a connector on the distal end of the elongate member that is larger than the appliance aperture, which prevents the connector from being passed through the appliance aperture (ii) the elongate member is comprises a tube, (iii) the appliance includes a suction port and a suction tubing connector, (iii) the connector connects to a suction handle, the suction handle having a switch for turning suction on and off and a suction tubing connector for attaching suction.

Example 3: The module of any of the foregoing examples, wherein (i) the appliance aperture has a circular cross section, (ii) the elongate member has a circular cross section, (iii) the tolerance between the elongate member and the appliance aperture is less than 0.05, 0.025, 0.015, 0.0075, or 0.0035, and/or greater than 0.0, 0.001, 0.0015, 0.003, 0.006, 0.012, inches and/or within a range of the foregoing endpoints (iv) the elongate member is rigid (v) the elongate member has a slidable sealing surface; (vi) the sliding seal surface has a length of at least 1, 2, 3, 4, or 5 inches and less than 15, 12, 10, or 8 inches (vii) the appliance has a fully retracted and fully extended position and the slidable sealing surface maintains the PPV seal at intermediate positions between fully extended and fully retracted positions (viii) at the intermediate positions the sealing surface and the aperture have a maximum gap of less than 0.05, 0.025, 0.015, 0.0075, or 0.0035, or greater than 0.0, 0.001, 0.0015, 0.003, 0.006, 0.012, inches and/or within a range of the foregoing endpoints; (ix) the elongate member with the slidable sealing surface is an extruded tube or an injection molded tube, (x) the tubing is injection molded and has a sloped inner diameter within the region of the sealing surface; (xi) working head has a maximum diameter less than 2, 1.5, 1.2, 0.8, or 0.6 and/or greater than 0.2, 0.5, 0.7, 1.0 or within a range of the foregoing; (xii) the working head has a minimum diameter less than 1.5, 1.2, 0.8, 0.6, or 0.4 and/or greater than 0.1, 0.2, 0.3, 0.5, or 0.7, or within a range of the foregoing.

Example 4: The appliance module of any of the foregoing examples wherein the appliance adapter includes a receptacle that the working head can be retracted into during attachment of the adapter to an access port.

Example 5: The appliance module of any of the foregoing examples, wherein the appliance is or includes (i) a suction appliance, (ii) a capnometry sampling line, (iii) a microphone, (iv) a yankauer, (v) a suction swab, or (vi) a suction brush. The appliance may also be single use or disposable (i.e., not manufactured for cleaning between patients).

Example 6: The appliance module of any of the foregoing examples, further comprising a lock feature configured to lock an adapter against axial movement of the appliance in the aperture until the lock is released.

Adapter Examples

Example 7: An appliance module as in any of the foregoing examples, wherein the adapter (i) seals with a ring connected to the PPV mask (ii) the ring secures the valve to the shell or elbow of the mask, (iii) the ring includes a lock feature for locking the adapter to the ring, (iv) the lock feature is a bayonet lock, (v) has a rib that mates with the ring, (vi) wherein the rib is chamfered, (vii) wherein the rib is less than 0.1 or 0.05 inch (viii) has the aperture formed in a housing member, (ix) wherein the housing member is a septum (x) housing member is injection molded with a housing wall of the adapter (xi) housing member forms a proximal end to a receptacle formed in the inside portion of the adapter; (xii) the housing member has a minimum thickness less than 0.5, 0.02, or 0.01 inch, (xiii) the length of the adapter from the seal structure to an oral end is at least 0.3, 0.6, 1.2, 2.4, or 5 inches and/or less than 8, 6, 4, 2, 1.5, 1, 0.6, or 0.3 inch and/or within a range of any of the foregoing endpoints, (xiv) the PPV seal is formed between surfaces of the adapter and access port having a gap less than 0.02, 0.015, 0.01, 0.006, or 0.003 and at or greater than 0.0, 0.001, 0.002, 0.003, 0.005, 0.006, 0.01 inch or within a range of the foregoing endpoints (xv) the inside portion has a maximum or minimum outer diameter less than 3, 2, 1.5, 1.2, or 0.6 inch and/or greater than 0.3, 0.6, 0.8, 1.0, 1.5 inch and/or within a range of the foregoing endpoints.

Suction Swab Examples: Example 8: The appliance module of any of the foregoing examples, wherein the working head (i) comprises a swab, (ii) the swab comprises a sponge material, (iii) the swab is adhered to the tubing (iv) the tubing is an extruded stick, (v) the swab is configured to engage the adapter when a user pulls on the tubing or a connector attached thereto to pull the adapter out of an access port by the tubing.

Suction Brush Examples: Example 9: The module as in any of the foregoing examples wherein (i) the suction appliance includes a suction brush, (ii) the working head of the suction brush is a brush head with a plurality of bristles extending therefrom, (iii), at least one, or preferably at least two suction inlets are formed in the brush head, (iv) the bristles are formed from bundles of fibers placed in a body of the brush head (e.g., U.S. Pat. Nos. 3,256,545 and 4,167,794), or are injected molded elements extending molded with the brush head (v) the brush head includes foam positioned on the head opposite the bristles, (v) a suction inlet is positioned through the foam.

Example 10: The module as in any of the foregoing examples, wherein (i) the suction brush head has a tubing connector (ii) the elongate tube is fixedly attached in the tubing connector, (iii) the tubing connector comprising a cylinder, (iv) the tubing connector has a depth of at least 0.05, 0.1, 0.15, or 0.2 and/or less than 0.5, 0.3, 0.25, or 0.2 inch or within a range of any of the foregoing endpoints.

Example 11: The appliance module of any of the foregoing examples, wherein the working head includes a suction brush; the brush adapter includes a receptacle configured to house the brush and an aperture centrally located at a proximal end of the receptacle; the suction brush includes a suction head with an elongate tubing connected to the head; the elongate tubing is centrally located on a proximal end of the head (i.e., the end closest to the aperture of the adapter) such that the adapter aperture and the suction brush tubing align axially. In some embodiments, the longitudinal axis of the tubing connector is off center from the midpoint of the brush head by less than 30%, 20%, 10%, or 5% in width and/or height.

Yankauer Examples: Example 12: The module of any of the forgoing examples, wherein the working head (i) includes a plurality of suction inlets at or near the distal end thereof, (ii) the plurality of inlets are in fluid communication with each other, (iii) the distal end includes a soft tip with a softer material than the elongate tubing, (iv) the distal end has a plurality of ribs that capture the working head in a retracted position (v) the working head has a stop feature inhibits movement through the aperture, (vi) the adapter includes a cover, (vii) the cover includes a plurality of ribs that capture the working head of the appliance in the retracted/covered position or (viii) combinations thereof.

Oral Care Kit Examples: Example 13: An oral care kit comprising (i) a plurality of appliance modules of any of the foregoing examples, (ii) a plurality of the same type and/or different types of suction appliance modules, (iii) one of or a plurality of suction swab modules, (iv) one of or a plurality of suction brush modules, (v) one of or a plurality of swab applicators, (vi) one of or a plurality of oral rinse solutions, (vii) one of or a plurality of antiplaque solution (viii) one of or a plurality of solutions with an active agent selected from cetylpyridinium chloride, hydrogen peroxide, or chlorhexidine, or a (ix) a suction handle, (x) individual treatment packages for performing a plurality of cleanings within a period of time (e.g., daily period), (xi) or combinations of these. The kit may also include a suction handle and/or have a connector with a suction port (e.g., thumb activated suction port).

Example 14: The oral care kit as in any of the foregoing examples comprising a plurality of individual packages, wherein at least a portion of the individual packages include an oral appliance and an oral rinse solution, the oral rinse solution packaged in a compartment of the individual package, wherein (i) the individual packaging has tray with first and second compartments, the first compartment housing the appliance and the second compartment housing the oral rinse (ii) a peel member covers the first and second compartments and peeling the cover exposes the appliance and at least a portion of the second compartment, thereby providing access to the oral rinse (iii) the first and second compartments have a perimeter seal that is stronger than a divider seal between the first and second compartments, (iv) a third compartment is positioned between the first and second components (v) the oral rinse is packaged in a sachet with a frangible seal (vi) the oral rinse is packaged in a cup with a peal cover.

Adapter Examples: Example 15: An appliance module as in any of the foregoing examples, wherein the adapter (i) seals with a ring connected to the PPV mask (ii) the ring secures the valve to the shell or elbow of the mask, (iii) the ring includes a lock feature for locking the adapter to the ring, (iv) the lock feature is a bayonet lock, (v) has a rib that mates with the ring, (vi) wherein the rib is chamfered, (vii) wherein the rib is less than 0.1 or 0.05 inch (viii) has the aperture formed in a membrane, wherein the membrane is (i) injection molded, (ii) an injection molded structure of an injection molded adapter (iii) has a thickness less than 0.5, 0.02, 0.01 inch.

Ventilator Examples: Example 16: A positive pressure ventilation system, comprising a ventilator control module including one or more processes and computer executable instruction that when executed on the one or more processors cause the module to: (i) receive detected pressure input from a positive pressure ventilation circuit, the circuit including a PPV mask; (ii) analyze the pressure input for a suction pressure signal indicative of changes in pressure caused by operation of a suction appliance in the PPV mask; and (iii) generate an output signal for driving a pressure generating system using at least in part the detected suction pressure signal.

Example 17: The ventilation system as in any of the foregoing examples wherein (i) the control module filters out at least a portion of the suction pressure signal, (ii) wherein the suction pressure is detected from a pressure signature that has changes in the rise, fall, rate of change, and/or duration in change of pressure that is different than a breathing pressure signature for rise, fall, and/or duration in change of pressure, or (iii) combinations thereof.

Example 18: A positive pressure ventilation system, comprising a ventilator control module including one or more processes and computer executable instruction that when executed on the one or more processors cause the module to: (i) receive detected pressure input from a positive pressure ventilation circuit, the circuit including a PPV mask; (ii) display to a user a selectable oral care setting and receiving input from the user indicating selection of the oral care setting; (iii) upon receiving input of the oral care setting being selected, adjusting a parameter of the ventilator.

Example 19: The system as in any of the foregoing, wherein (i) the adjusted parameter is an alarm setting, an iPAP setting, and/or a ePAP setting, wherein (ii) the alarm setting is set to increase a leak rate at which an alarm is triggered, (iii) the alarm has a duration parameter that limits the change in the parameter to a particular amount of time, (iv) the duration parameter is less than 20, 15, 10, or 5 minutes and/or greater than 1, 3, 5, or 10 minutes or within a range thereof, (v) iPAP is reduced, (vi) a pressure at which iPAP is triggered is reduced, (vii), the pressure at which ePAP is trigger is reduced, (vii) the rate of change in pressure needed to trigger ePAP or iPAP is increased, or (ix) combinations of the foregoing.

Example 20: The system as in any of the foregoing, wherein the suction appliance and/or the PPV mask are as in any of the forgoing examples.

Example 21: A PPV system comprising: a PPV mask with an access port; an appliance module, an oral care appliance module, a suction appliance module, a capnometry module, endoscopy module, or a nebulizer module as in any of the examples herein, wherein the module forms the first seal with the access port of the PPV mask, (i) wherein the module includes an adapter that forms the first seal with the access port.

Example 22: The PPV system as in any of the foregoing examples, wherein (i) the access port is provided by an elbow connector of the mask, (ii) the access port is flexibly connected to a shell of the mask, (iii) wherein the flexible connection is provided by mask a flexible shell region, (iv) wherein the flexible connection is provided by a flexible connector between the access port and the shell, (v) or combinations of these.

Example 23: A method for performing oral care, suctioning, oral cleaning, or brushing, comprising, providing a PPV system of any of the examples herein, connecting the adapter to the access port, introducing the working head of the appliance into the oral cavity, performing an oral procedure using the working head, removing the adapter from the access port. The method further comprising, one or more of suctioning, dipping the working head in a solution, and/or scrubbing. The method further comprising, withdrawing the working head into the adapter and/or pulling the adapter out of the access port by withdrawing the tubing from the adapter until the working head engages the adapter and forces the adapter from the access port.

Capnometry Examples. Example 24: A positive pressure ventilation (PPV) capnometry module, comprising: an elongate support housing sized and configured to be placed through an access port of a PPV mask, the support housing extending from an oral end to an external end opposite the oral end, the support housing sized and configured to be placed through an access port of an PPV mask and form a first PPV seal therewith, wherein with the support housing inserted and sealed, the oral end is positioned in the oral end of a patient wearing the mask and the external end is external to the mask; a capnometry sampling line positioned within the support housing and having a sampling inlet positioned at or near the oral end of the support housing, the sampling inlet in fluid communication with an exterior of the support housing for sampling oral gasses, the sampling line passing through an aperture in the support housing to the outside portion of the adapter and forming a second PPV seal with the elongate support housing or an adapter attached thereto, the sampling line having a line connector distal to the external end and configured to attach the sampling line to a capnometry system suitable for measuring end tidal $CO_2$ of a sampled gas.

Example 25: The capnometry module as in example 1, wherein the capnometry module is sized and configured to be inserted through (i) a slit valve positioned in an access port of the PPV mask, (ii) a valve that seals from ventilator pressure, (iii) or combinations of these.

Example 26: The capnometry module as in any of the foregoing examples, further comprising a PPV adapter having a first seal surface configured to form the first PPV seal with the access port of the PPV mask when attached thereto, the PPV adapter having an inside portion on a first side of the first seal surface and an outside portion on a second side opposite the first side, wherein the inside portion is exposed to the pressure of the ventilator and the outside portion is exposed to a pressure external to the PPV mask when the adapter is attached thereto.

Example 27: The capnometry module as in any of the foregoing examples, wherein the first seal surface is positioned a body of the adapter and the elongate housing is an extension of the adapter body or fixedly attached thereto, wherein the sampling line forms the second seal with the adapter body.

Example 28: The capnometry module as in any of the foregoing examples, wherein the first seal surface is provided by a body of the adapter and the support housing is slidably attached to the adapter body such that a depth of the oral end of the support housing is adjustable within the PPV mask relative to the adapter.

Example 29: The capnometry module as in any of the foregoing examples, wherein the support housing has a second end opposite the oral end, the support housing extending through an outside portion of the adapter to the second end and having a proximal connector that forms the second seal with the sampling line, the outside connector providing a grip surface suitable for a user to slidably adjust the depth of the support housing relative to the adapter body.

Example 30: The capnometry module as in any of the foregoing examples, wherein the support housing can be slidably adjusted to a covered position in which the sampling inlet of the oral end is positioned within a cover portion of the adapter body for storage and an extended position in which the sampling inlet of the oral end is extended for use in sampling exhalation gases in the oral cavity.

Example 31: The capnometry module as in any of the foregoing examples, wherein a first end of a sheath is connected to the adapter body and a second end of the sheath is connected to the second end of the support housing, the sheath being flexible such that it compresses when the support housing is moved from the covered position to the extended position.

Example 32: The capnometry module as in any of the foregoing examples further comprising a casing attached the support housing at or near the oral end, wherein the sampling inlet is formed in the casing wherein (i) the capnometry module as in any of the foregoing examples, wherein the casing is made from a softer material than the support housing (e.g., a rubber material); (ii) the support housing comprises tubing and the casing covers the tubing wall at the oral end; (iii) the housing tubing includes one or a plurality of apertures in the tubing wall that are positioned to allow exhalation gases to pass into and out of the housing tube when the mouth of the patient is sealed around the tubing; (iv) the sampling line has an internal diameter greater than 0.5, 0.8, or 1 mm and/or less than 5, 4, 3, 2, mm or within a range of the foregoing endpoints.

Example 33: A PPV system comprising: a PPV mask with an access port; and the capnometry module of any of the forgoing examples attached to the access port.

Example 34: The PPV system as in any of the forgoing examples, wherein (i) the PPV mask includes a valve in the access port (ii) the valve is a slit valve and the support housing seals with the slit valve, (iii) the valve is a self-sealing valve or a valve that seals under PPV, (iv) the module includes a capnometry adapter that seals with the access port (iii) the access port is positioned in a shell of the mask or an elbow connector of the mask.

Nebulizer Examples: Example 35: A positive pressure ventilation (PPV) nebulizer module, comprising: a nebulizer adapter having a first seal surface configured to form a PPV seal with an access port of a PPV mask when attached thereto, the nebulizer adapter having an inside portion on a first side of the first seal and an outside portion on a second side opposite the first side, wherein the inside portion is exposed to the pressure of the ventilator and the outside portion is exposed to a pressure external to the PPV mask when the adapter is attached thereto; a fluid reservoir formed in the module, the fluid reservoir having an inlet port that opens and closes for filling the reservoir with a nebulization fluid; a tubular structure defined by or connected to the inside portion of the adapter, at least a portion of the tubular structure positioned within the PPV mask when the adapter is attached thereto; the tubular structure having an oral end (either forming an opening or having the aerosol element generator positioned therein); a aerosol generator positioned in the tubular structure (optionally at an end of the tubular structure opposite the oral end), a first side of the vibrating element in fluid communication with the tubular structure (or positioned at the oral end) and a second opposite side of the vibrating element in fluid communication with the reservoir; a plurality of electrical leads connected to the vibrating element for receiving a signal to power the vibrating element.

Example 36: A nebulizer module as in any of the foregoing examples, wherein (i) the aerosol generator is positioned within the module such that the vibrating element is positioned within an elbow connector or a shell of the PPV mask when the adapter is attached thereto, (ii) the inlet port of the reservoir is positioned on the outside portion of the adapter; (iii) the inlet port is positioned on the inside portion of the adapter (iv) the reservoir has a sloped wall that ends in a recess at a base of the vibrating element; (v) a moisture sensor element within the reservoir (vi) the moisture sensor element positioned within the recess at the base of the vibrating element; (vii) the sealing surface of the adapter is configured to slidably connect with an opening of the access port; (viii) the opening having a circular cross-section, (ix) the adapter when attached to the mask is configured to open a valve in the access port, (x) the access port has a cross section with a minimum width and/or height (i.e., x and y) of at least 0.2, 0.3, 0.4, 0.5, 0.6, 0.8 inch and less than 2.0, 1.5, 1.25, or 1.0 inch and/or a range within the foregoing (xi) the opening has a cross section with a maximum width and/or height less 3.0, 2.0, 1.5, 1.25, or 1.0 and/or greater than 0.4, 0.6, 0.8, 1.0, 2.0, 3.0, (xiii) the adapter includes a lock feature that locks the adapter to the access port; (xiv) the lock feature is a bayonet lock, (xv) the adapter has a rib that mates with the ring, (xvi) wherein the rib is chamfered, (xvii) wherein the rib is less than 0.1 or 0.05 inch (xviii) the tubing structure is formed in a support housing that slidably connects to a body of the adapter, where the adapter body includes the seal (see capnometry adapter), (xix) the reservoir has a volume less than 50, 40, 30, or 25 ml and/or greater than 2, 4, 8, 12, or 20 ml and/or within a range of the foregoing, (xx) a wire connector for receiving nebulization control signal from a control module or (xxi) combinations of the foregoing.

Example 37: The nebulizer module as in any of the foregoing examples, wherein the adapter houses (i) a battery, (ii) a circuit board powered by the battery, (iii) the circuit board is configured to drive the nebulizer element, (iv) a nebulization on and/or off button, (v) LED indicator for battery and/or on/off, (vi) the button has haptic feedback to indicate on/off of nebulization and/or on/off of auto-off; the circuitry is configured to turn the circuitry off based on a lack of moisture as indicated by the moisture sensor, (vii) wherein the adapter extends a maximum of less than 3.0, 2.5, 2.0, 1.5, or 1.0 inches from the access port when the adapter is attached thereto.

Example 38: A positive pressure ventilation (PPV) nebulizer system, comprising: a PPV mask comprising a shell and a cushion, the cushion having a membrane configured to seal with a face under positive pressure from a ventilator, the shell having an access port with a valve that seals under pressure from the ventilator; a PPV nebulizer adapter that removably connects to the access port of the mask and opens the valve when connected thereto, the adapter including a tubular structure that provides a fluid pathway for nebulized gases through the valve when attached to the access port; a nebulizer in fluid communication with the tubular structure of the adapter, the nebulizer including a fluid reservoir, a nebulizer module, and a conduit for delivering nebulized gasses from the nebulizer module to the tubular structure of the adapter.

Example 39: The nebulizer system of any of the foregoing examples, wherein (i) the nebulizer module includes a sonication disc, (ii) the sonication disc includes a vibrating element, (iii) the sonication disc is powered by a battery, (iv) the nebulizer module is portable and integrated into the adapter, (v) the nebulizer module connects to a source of air that is forced through fluids from the reservoir to cause nebulization, (v) and combinations of these.

Example 40: The nebulizer system of any of the foregoing examples, wherein (i) the access port is formed in an elbow connector of the mask, (ii) the valve is a cross-slit valve and/or a duck bill valve, and/or (iii) combinations of these.

Example 41: A nebulizer adapter as in any of the foregoing examples.

Example 42: A method for performing nebulization, comprising, providing a nebulization system as in any of the foregoing examples, introducing a nebulizable fluid into the fluid reservoir of the nebulizer module, nebulizing the fluid using the nebulizer apparatus, and delivering the nebulized fluid into the mask while providing pressure in the mask from a ventilator connected thereto.

Endoscopy Examples

Example 43: A positive pressure ventilation (PPV) endoscopy system, comprising: a PPV mask comprising a shell and a cushion, the cushion having a membrane configured to seal with a face under positive pressure from a ventilator, the shell having an access port with a valve that seals under pressure from the ventilator; a PPV endoscopy adapter that removably connects to the access port and opens the valve when connected thereto, the adapter including a tubular structure that has a valve positioned therein, the valve being configured to form a slidable seal with an endoscope.

Example 44: The endoscopy system of any of the foregoing examples, wherein (i) the access port is formed in an elbow connector of the mask, (ii) the valve is a cross-slit valve and/or a duck bill valve, (iii) the valve is over molded in an injection molded process with the adaptor, or (iv) combinations of these.

Example 45: The endoscopy system as in any of the foregoing examples, wherein the adapter further comprises a bite block; (i) wherein the bite block extends through the adapter or forms an integral part of the adapter (ii) the bite block is sufficiently long to pass between the teeth of a patient when the adapter is positioned in the access port.

Example 46: An endoscopy adapter as in any of the foregoing examples.

A method for performing an endoscopy procedure, comprising, providing an endoscopy system as in any of the foregoing examples, introducing the endoscopy adapter in the PPV mask and introducing an endoscope in the endoscopy adapter under pressure from a ventilator connected to the PPV mask.

We claim:

1. A method for providing oral care through a positive pressure ventilation (PPV) mask, comprising:

providing a PPV mask having an access port sized and configured to pass therethrough a working head of a swab device or a toothbrush;

providing an oral care module comprising an oral care appliance assembled with a PPV appliance adapter, the oral care appliance having an elongate member and a working head forming a swab device or a toothbrush, wherein,
  (i) the PPV appliance adapter is configured to be removably attached to the access port of the PPV mask and form a first PPV seal therewith;
  (ii) the PPV appliance adapter defines an aperture that forms a second PPV seal with the elongate member, the appliance adapter having an inside portion on a first side of the aperture and an outside portion on a second side opposite the first side, wherein the inside portion is exposed to the pressure of the ventilator and the outside portion is exposed to a pressure external to the PPV mask when the adapter is attached thereto; and
  (iii) the working head is positioned on the inside portion of the appliance adapter and has a larger diameter than the elongate member and the aperture;
applying a cleaning fluid or a moisturizer to the working head of the oral care module and thereafter attaching the appliance adapter to the access port of the PPV mask and advancing the working head therethrough.

2. The method of claim 1, wherein elongate member is slidable within the appliance aperture so as to allow the working head to be extended and retracted within the PPV mask when the adapter is attached thereto.

3. The method of claim 2, wherein the elongate member has a sliding sealing surface of at least 2 inches and less than 12 inches.

4. The method of claim 3, wherein the appliance aperture and the sliding sealing surface have a tolerance in a range from 0.003 inch to 0.025 inch at an intermediate position of the appliance being fully retracted and fully extended in the appliance aperture.

5. The method of claim 1, wherein the oral care appliance includes an elongate member with a fluid channel in fluid communication with the working head and a connector for attaching a source of suction to the oral care appliance.

6. The method of claim 1, wherein the elongate member comprises a tube with a circular cross section.

7. The method of claim 1, wherein the maximum diameter of the working head is in a range from 0.3-1.5 inch.

8. The method as in claim 1, wherein the port includes a duckbill valve.

9. The method of claim 1, wherein the oral care appliance is a suction swab device and the applying step includes applying a cleaning fluid that includes an antimicrobial, the method further comprising using the working head of the suction swab device to perform a cleaning procedure through the port while maintaining a pressure of at least 4 cm $H_2O$ in the PPV mask, then suctioning the oral cavity of the patient, and then removing the working head of the suction swab device from the PPV mask and detaching the adapter from the access port.

10. The method of claim 1, wherein the oral care appliance is a swab device, the method further comprising:
  while maintaining a pressure of at least 4 cm $H_2O$ in the PPV mask, swabbing the oral cavity of a patient wearing the mask, then then removing the working head from the PPV mask, and detaching the adapter from the access port.

11. The method of claim 1, further comprising cleaning the teeth of the patient using the working head while maintaining a pressure of at least 4 cm $H_2O$ in the PPV mask and thereafter removing the oral care appliance from the oral cavity and detaching the adapter from the access port.

12. A positive pressure ventilation (PPV) oral care module for performing an oral care procedure through a PPV mask, comprising:
  an oral care appliance comprising a toothbrush or swab device, the oral care appliance including a working head and an elongate member;
  a PPV appliance adapter configured to be removably attached to an access port of a PPV mask, the appliance adapter having a first seal surface configured to form a first PPV seal with an access port of the PPV mask when attached thereto, the appliance adapter having a septum defining an aperture, the elongate member positioned in the aperture and forming a second PPV seal therewith, the septum having a minimum thickness less than 0.5 inches that enables articulation of the elongate member, the appliance adapter having an inside portion on a first side of the septum and an outside portion on a second side opposite the first side, wherein the inside portion is exposed to the pressure of the ventilator and the outside portion is exposed to a pressure external to the PPV mask when the appliance adapter is attached thereto, the working head positioned on the inside portion of the appliance adapter and having a diameter greater than the aperture and the elongate member.

13. The oral care module of claim 12, wherein the adapter includes a receptacle for housing at least a majority of the working head.

14. The oral care module of claim 13, wherein the working head includes foam.

15. The oral care module of claim 12, wherein the second PPV seal is formed by a gap between the aperture and the elongate member with a tolerance in a range from 0.003 inch to 0.025 inch with the appliance positioned at an intermediate position between fully extended and fully retracted relative to the adapter.

16. The oral care module of claim 12, wherein the septum has a minimum thickness less than 0.1 inch.

17. The oral care module of claim 12, wherein the elongate member comprises a suction tube with a fluid channel in fluid communication with the working head, wherein the oral care appliance further comprises a connector for attaching suction thereto.

18. A positive pressure ventilation (PPV) oral care module for performing an oral care procedure through a PPV mask, comprising:
  swab device comprising a foam working head positioned at a first end of a tubular shaft;
  a PPV appliance adapter configured to be removably attached to an access port of a PPV mask, the appliance adapter comprising a housing having a first seal surface configured to form a first PPV seal with the access port, the housing defining a receptacle having a wall that defines an aperture, the tubular shaft positioned in the aperture and forming a second PPV seal therewith, the shaft slidable within aperture between a retracted position in which the foam working head is positioned in the receptacle and an extended position in which the foam is removed from the receptacle, the wall having a minimum thickness of less than 0.5 inch, the appliance adapter having an inside portion on a first side of the wall and an outside portion on a second side opposite the first side, wherein the inside portion is exposed to the pressure of the ventilator and the outside portion is exposed to a pressure external to the PPV mask when the adapter is attached thereto, the working head positioned on the inside portion of the adapter and having a diameter greater than the aperture and the elongate member.

19. The oral care module of claim 18, wherein the housing is a single injection molded piece and the wall has a minimum thickness less than 0.1 inch.

20. The oral care module of claim 19, wherein the second PPV seal is formed by a gap between the aperture and the elongate member with a tolerance in a range from 0.003 inch to 0.025 inch with the oral care appliance positioned at an intermediate position between fully extended and fully retracted relative to the adapter.

* * * * *